(12) United States Patent
Plough et al.

(10) Patent No.: US 8,464,708 B2
(45) Date of Patent: Jun. 18, 2013

(54) PNEUMOSTOMA MANAGEMENT SYSTEM HAVING A COSMETIC AND/OR PROTECTIVE COVER

(75) Inventors: David C. Plough, Portola Valley, CA (US); Don Tanaka, Saratoga, CA (US); Joshua P. Wiesman, Boston, MA (US); Jeffrey C. Cerier, Franklin, MA (US); Richard A. Abraham, Reading, MA (US); Stephen C. Evans, Westford, MA (US); Gary L. Boseck, Belmont, CA (US)

(73) Assignee: Portaero, Inc., Cupertino, CA (US)

( * ) Notice: Subject to any disclaimer, the term of this patent is extended or adjusted under 35 U.S.C. 154(b) by 1139 days.

(21) Appl. No.: 12/388,460

(22) Filed: Feb. 18, 2009

(65) Prior Publication Data

US 2009/0205647 A1 Aug. 20, 2009

Related U.S. Application Data

(60) Provisional application No. 61/029,830, filed on Feb. 19, 2008, provisional application No. 61/032,877, filed on Feb. 29, 2008, provisional application No. 61/038,371, filed on Mar. 20, 2008, provisional application No. 61/082,892, filed on Jul. 23, 2008, provisional application No. 61/083,573, filed on Jul. 25, 2008, provisional application No. 61/084,559, filed on Jul. 29, 2008, provisional application No. 61/088,118, filed on Aug. 12, 2008, provisional application No. 61/143,298, filed on Jan. 8, 2009, provisional application No. 61/151,581, filed on Feb. 11, 2009.

(51) Int. Cl.
*A61M 16/00* (2006.01)
*A61M 5/00* (2006.01)

(52) U.S. Cl.
USPC ............ 128/200.24; 128/202.27; 128/205.12; 128/205.19; 128/205.24; 604/45; 604/174; 604/175; 604/180; 604/304; 604/307; 604/386

(58) Field of Classification Search
USPC ............. 128/200.24, 200.25, 202.27, 205.12, 128/205.19, 205.24; 604/45, 174, 175, 180, 604/304, 307, 386
See application file for complete search history.

(56) References Cited

U.S. PATENT DOCUMENTS

| 733,152 A | 7/1903 | Chisholm |
| 953,922 A | 4/1910 | Rogers |

(Continued)

FOREIGN PATENT DOCUMENTS

| EP | 0260543 A1 | 3/1988 |
| EP | 1358904 | 5/2003 |

(Continued)

OTHER PUBLICATIONS

Extended European Search Report dated Jun. 22, 2011 for PCT/US2009034374, 7 pages.

(Continued)

*Primary Examiner* — Clinton T Ostrup
(74) *Attorney, Agent, or Firm* — Fliesler Meyer LLP

(57) ABSTRACT

A pneumostoma management system which includes a pneumostoma management device and a cover. The pneumostoma management device maintains the patency of a pneumostoma while controlling the flow of material through the pneumostoma. The pneumostoma management device includes a hydrophobic filter and/or a one-way filter. The cover serves to protect the pneumostoma management device and/or provide a cosmetic skin to make the pneumostoma management device more acceptable to the patient and thereby encourage patient compliance with a pneumostoma treatment regimen.

20 Claims, 9 Drawing Sheets

U.S. PATENT DOCUMENTS

| | | | |
|---|---|---|---|
| 2,206,687 A | 7/1940 | Bloomheart | |
| 2,867,213 A | 1/1959 | Thomas, Jr. | |
| 2,873,742 A | 2/1959 | Shelden | |
| 2,991,787 A | 7/1961 | Shelden et al. | |
| 3,253,594 A | 5/1966 | Matthews et al. | |
| 3,384,087 A | 5/1968 | Brummelkamp | |
| 3,463,159 A | 8/1969 | Heimlich | |
| 3,511,243 A | 5/1970 | Toy | |
| 3,556,103 A | 1/1971 | Calhoun et al. | |
| 3,638,649 A | 2/1972 | Ersek | |
| 3,682,166 A | 8/1972 | Jacobs | |
| 3,688,773 A | 9/1972 | Weiss | |
| 3,707,146 A | 12/1972 | Cook et al. | |
| 3,766,920 A | 10/1973 | Greene | |
| 3,777,757 A | 12/1973 | Gray et al. | |
| 3,788,326 A | 1/1974 | Jacobs | |
| 3,817,250 A | 6/1974 | Weiss et al. | |
| 3,908,704 A | 9/1975 | Clement et al. | |
| 3,916,903 A | 11/1975 | Pozzi | |
| 4,153,058 A | 5/1979 | Nehme | |
| 4,291,694 A | 9/1981 | Chai | |
| 4,439,189 A | 3/1984 | Sargeant et al. | |
| 4,465,062 A * | 8/1984 | Versaggi et al. | 128/897 |
| 4,502,482 A | 3/1985 | DeLuccia et al. | |
| 4,583,977 A | 4/1986 | Shishov et al. | |
| 4,657,006 A * | 4/1987 | Rawlings et al. | 602/47 |
| 4,664,660 A | 5/1987 | Goldberg et al. | |
| 4,799,494 A | 1/1989 | Wang | |
| 4,813,929 A | 3/1989 | Semrad | |
| 4,826,495 A | 5/1989 | Petersen | |
| 4,828,553 A | 5/1989 | Nielsen | |
| 4,869,717 A | 9/1989 | Adair | |
| 4,872,869 A | 10/1989 | Johns | |
| 4,889,534 A | 12/1989 | Mohiuddin et al. | |
| 4,931,045 A | 6/1990 | Steer | |
| 4,944,724 A | 7/1990 | Goldberg et al. | |
| 4,959,054 A | 9/1990 | Heimke et al. | |
| 4,976,688 A | 12/1990 | Rosenblum | |
| 5,004,456 A | 4/1991 | Botterbusch et al. | |
| 5,060,645 A | 10/1991 | Russell | |
| 5,078,689 A | 1/1992 | Keller | |
| 5,137,509 A | 8/1992 | Freitas | |
| 5,139,485 A | 8/1992 | Smith et al. | |
| 5,218,957 A | 6/1993 | Strickland | |
| 5,230,332 A | 7/1993 | Strickland | |
| 5,230,350 A * | 7/1993 | Fentress | 128/846 |
| D340,987 S * | 11/1993 | Arginsky | D24/189 |
| D340,989 S * | 11/1993 | Arginsky | D24/189 |
| 5,261,708 A | 11/1993 | Steer | |
| 5,263,939 A | 11/1993 | Wortrich | |
| 5,312,331 A | 5/1994 | Knoepfler | |
| 5,315,992 A | 5/1994 | Dalton | |
| 5,336,206 A | 8/1994 | Shichman | |
| 5,354,283 A | 10/1994 | Bark et al. | |
| 5,356,386 A | 10/1994 | Goldberg et al. | |
| 5,366,478 A | 11/1994 | Brinkerhoff et al. | |
| 5,370,625 A | 12/1994 | Shichman | |
| 5,376,376 A | 12/1994 | Li | |
| 5,389,077 A | 2/1995 | Melinyshyn et al. | |
| 5,401,262 A | 3/1995 | Karwoski et al. | |
| 5,403,264 A | 4/1995 | Wohlers et al. | |
| 5,431,633 A | 7/1995 | Fury | |
| 5,478,333 A | 12/1995 | Asherman, Jr. | |
| 5,484,401 A | 1/1996 | Rodriguez et al. | |
| 5,496,297 A | 3/1996 | Olsen | |
| 5,501,677 A | 3/1996 | Jensen | |
| 5,501,678 A | 3/1996 | Olsen | |
| 5,588,424 A | 12/1996 | Insler et al. | |
| 5,616,131 A | 4/1997 | Sauer et al. | |
| 5,660,175 A | 8/1997 | Dayal | |
| 5,662,629 A | 9/1997 | Steer et al. | |
| 5,666,950 A * | 9/1997 | Smith | 128/207.14 |
| 5,728,066 A | 3/1998 | Daneshvar | |
| 5,730,735 A | 3/1998 | Holmberg et al. | |
| 5,738,661 A | 4/1998 | Larice | |
| 5,807,341 A | 9/1998 | Heim | |
| 5,830,200 A | 11/1998 | Steer et al. | |
| 5,843,053 A | 12/1998 | Steer | |
| 5,897,531 A * | 4/1999 | Amirana | 604/180 |
| 5,931,821 A | 8/1999 | Weilbacher et al. | |
| 5,954,636 A | 9/1999 | Schwartz et al. | |
| 5,971,962 A | 10/1999 | Kojima et al. | |
| 5,972,026 A | 10/1999 | Laufer et al. | |
| 6,056,744 A | 5/2000 | Edwards | |
| 6,059,816 A | 5/2000 | Moenning | |
| 6,083,255 A | 7/2000 | Laufer et al. | |
| 6,174,323 B1 | 1/2001 | Biggs et al. | |
| 6,197,010 B1 | 3/2001 | Leise, Jr. et al. | |
| 6,200,333 B1 | 3/2001 | Laufer | |
| 6,222,090 B1 * | 4/2001 | Weston | 602/41 |
| 6,258,100 B1 | 7/2001 | Alferness et al. | |
| 6,273,907 B1 | 8/2001 | Laufer | |
| 6,274,787 B1 * | 8/2001 | Downing | 602/41 |
| 6,283,988 B1 | 9/2001 | Laufer et al. | |
| 6,283,989 B1 | 9/2001 | Laufer et al. | |
| 6,287,290 B1 | 9/2001 | Perkins et al. | |
| 6,293,930 B1 | 9/2001 | Brunsgaard et al. | |
| 6,293,951 B1 | 9/2001 | Alferness et al. | |
| 6,299,633 B1 | 10/2001 | Laufer | |
| 6,322,536 B1 | 11/2001 | Rosengart et al. | |
| 6,328,689 B1 | 12/2001 | Gonzalez et al. | |
| 6,330,882 B1 | 12/2001 | French | |
| 6,334,441 B1 | 1/2002 | Zowtiak et al. | |
| 6,358,269 B1 | 3/2002 | Aye | |
| 6,398,775 B1 | 6/2002 | Perkins et al. | |
| 6,402,754 B1 | 6/2002 | Gonzalez | |
| 6,411,852 B1 | 6/2002 | Danek et al. | |
| 6,416,554 B1 | 7/2002 | Alferness et al. | |
| 6,432,100 B1 | 8/2002 | Affeld | |
| 6,443,156 B1 | 9/2002 | Niklason et al. | |
| 6,459,917 B1 * | 10/2002 | Gowda et al. | 600/345 |
| 6,468,292 B1 | 10/2002 | Mollenauer et al. | |
| 6,485,407 B2 | 11/2002 | Alferness et al. | |
| 6,488,673 B1 | 12/2002 | Laufer et al. | |
| 6,491,706 B1 | 12/2002 | Alferness et al. | |
| 6,514,290 B1 | 2/2003 | Loomas | |
| 6,517,519 B1 | 2/2003 | Rosen et al. | |
| 6,520,183 B2 | 2/2003 | Amar | |
| 6,527,761 B1 | 3/2003 | Soltesz et al. | |
| 6,550,475 B1 | 4/2003 | Oldfield | |
| 6,569,121 B1 | 5/2003 | Purow et al. | |
| 6,569,166 B2 | 5/2003 | Gonzalez | |
| 6,585,639 B1 | 7/2003 | Kotmel et al. | |
| 6,589,161 B2 | 7/2003 | Corcoran | |
| 6,592,594 B2 | 7/2003 | Rimbaugh et al. | |
| 6,599,311 B1 | 7/2003 | Biggs et al. | |
| 6,609,521 B1 | 8/2003 | Belani et al. | |
| 6,629,951 B2 | 10/2003 | Laufer et al. | |
| 6,632,239 B2 | 10/2003 | Snyder et al. | |
| 6,632,243 B1 | 10/2003 | Zadno-Azizi et al. | |
| 6,634,360 B1 | 10/2003 | Flodin | |
| 6,634,363 B1 | 10/2003 | Danek et al. | |
| 6,638,253 B2 | 10/2003 | Breznock | |
| 6,653,525 B2 | 11/2003 | Ingenito et al. | |
| 6,659,961 B2 | 12/2003 | Robinson | |
| 6,679,264 B1 | 1/2004 | Deem et al. | |
| 6,682,506 B1 | 1/2004 | Navarro | |
| 6,692,494 B1 | 2/2004 | Cooper et al. | |
| 6,694,979 B2 | 2/2004 | Deem et al. | |
| 6,695,791 B2 | 2/2004 | Gonzalez | |
| 6,709,401 B2 | 3/2004 | Perkins et al. | |
| 6,712,812 B2 | 3/2004 | Roschak et al. | |
| 6,736,797 B1 * | 5/2004 | Larsen et al. | 604/167.05 |
| 6,749,606 B2 | 6/2004 | Keast et al. | |
| 6,770,063 B2 | 8/2004 | Goldberg et al. | |
| 6,770,070 B1 | 8/2004 | Balbierz | |
| 6,790,172 B2 | 9/2004 | Alferness et al. | |
| 6,827,086 B2 | 12/2004 | Shuman | |
| 6,837,906 B2 | 1/2005 | Ginn | |
| 6,840,243 B2 | 1/2005 | Deem et al. | |
| 6,843,767 B2 | 1/2005 | Corcoran et al. | |
| 6,846,292 B2 | 1/2005 | Bakry | |
| 6,849,061 B2 | 2/2005 | Wagner | |
| 6,852,108 B2 | 2/2005 | Barry et al. | |
| 6,860,847 B2 | 3/2005 | Alferness et al. | |
| 6,878,141 B1 | 4/2005 | Perkins et al. | |
| 6,886,558 B2 | 5/2005 | Tanaka | |

| | | |
|---|---|---|
| 6,901,927 B2 | 6/2005 | Deem et al. |
| 6,904,909 B2 | 6/2005 | Andreas et al. |
| 6,905,518 B2 | 6/2005 | Ginn |
| 6,916,310 B2 | 7/2005 | Sommerich |
| 6,929,637 B2 | 8/2005 | Gonzalez et al. |
| 6,941,950 B2 | 9/2005 | Wilson et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,014,628 B2 | 3/2006 | Bousquet |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |
| 7,086,398 B2 | 8/2006 | Tanaka |
| 7,100,616 B2 | 9/2006 | Springmeyer |
| 7,135,010 B2 | 11/2006 | Buckman et al. |
| 7,141,046 B2 | 11/2006 | Perkins et al. |
| 7,165,548 B2 | 1/2007 | Deem et al. |
| 7,172,581 B2 | 2/2007 | Ciok et al. |
| 7,175,644 B2 | 2/2007 | Cooper et al. |
| 7,182,772 B2 | 2/2007 | Alferness et al. |
| 7,186,259 B2 | 3/2007 | Perkins et al. |
| 7,192,420 B2 | 3/2007 | Whiteford |
| 7,195,016 B2 | 3/2007 | Loyd et al. |
| 7,195,017 B2 | 3/2007 | Tanaka |
| 7,207,946 B2 | 4/2007 | Sirokman |
| 7,232,414 B2 | 6/2007 | Gonzalez |
| 7,244,245 B2 | 7/2007 | Purow et al. |
| 7,252,086 B2 | 8/2007 | Tanaka |
| 7,377,278 B2 | 5/2008 | Tanaka |
| 7,398,782 B2 | 7/2008 | Tanaka |
| 7,406,963 B2 | 8/2008 | Chang et al. |
| 7,426,929 B2 | 9/2008 | Tanaka |
| 7,533,667 B2 | 5/2009 | Tanaka |
| 2001/0020145 A1* | 9/2001 | Satterfield et al. ............... 604/24 |
| 2001/0025132 A1 | 9/2001 | Alferness et al. |
| 2001/0041906 A1 | 11/2001 | Gonzalez |
| 2001/0041932 A1 | 11/2001 | Scholz et al. |
| 2002/0042564 A1 | 4/2002 | Cooper et al. |
| 2002/0062120 A1 | 5/2002 | Perkins et al. |
| 2002/0077593 A1 | 6/2002 | Perkins et al. |
| 2002/0087153 A1 | 7/2002 | Roschak et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0120177 A1 | 8/2002 | Borst et al. |
| 2002/0165618 A1 | 11/2002 | Ingenito et al. |
| 2002/0188171 A1 | 12/2002 | Alferness et al. |
| 2003/0013935 A1 | 1/2003 | Alferness et al. |
| 2003/0018344 A1 | 1/2003 | Kaji et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0065339 A1 | 4/2003 | Snyder et al. |
| 2003/0069488 A1 | 4/2003 | Alferness et al. |
| 2003/0078469 A1 | 4/2003 | Corcoran |
| 2003/0083542 A1 | 5/2003 | Alferness et al. |
| 2003/0083671 A1 | 5/2003 | Rimbaugh et al. |
| 2003/0127090 A1 | 7/2003 | Gifford et al. |
| 2003/0130593 A1 | 7/2003 | Gonzalez |
| 2003/0149446 A1 | 8/2003 | Shuman |
| 2003/0154988 A1 | 8/2003 | DeVore et al. |
| 2003/0158515 A1 | 8/2003 | Gonzalez et al. |
| 2003/0163024 A1 | 8/2003 | Corcoran |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0186904 A1 | 10/2003 | Ruben et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0216730 A1 | 11/2003 | Barry et al. |
| 2003/0216769 A1 | 11/2003 | Dillard et al. |
| 2003/0228344 A1 | 12/2003 | Fields et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0016435 A1 | 1/2004 | Deem et al. |
| 2004/0024356 A1 | 2/2004 | Tanaka |
| 2004/0031494 A1 | 2/2004 | Danek et al. |
| 2004/0040555 A1 | 3/2004 | Tanaka |
| 2004/0047855 A1 | 3/2004 | Ingenito |
| 2004/0055606 A1 | 3/2004 | Hendricksen et al. |
| 2004/0059263 A1 | 3/2004 | DeVore et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078026 A1 | 4/2004 | Wagner |
| 2004/0078054 A1 | 4/2004 | Biggs et al. |
| 2004/0087831 A1 | 5/2004 | Michels et al. |
| 2004/0097983 A1 | 5/2004 | Snyder et al. |
| 2004/0143282 A1 | 7/2004 | Dillard et al. |
| 2004/0144387 A1 | 7/2004 | Amar |
| 2004/0158228 A1 | 8/2004 | Perkins et al. |
| 2004/0167636 A1 | 8/2004 | Dillard et al. |
| 2004/0173218 A1 | 9/2004 | Yamada et al. |
| 2004/0199128 A1 | 10/2004 | Morris et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0211412 A1 | 10/2004 | Alferness et al. |
| 2004/0211434 A1 | 10/2004 | Loomas et al. |
| 2004/0220446 A1 | 11/2004 | Corcoran et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0237966 A1 | 12/2004 | Tanaka |
| 2004/0243140 A1 | 12/2004 | Alferness et al. |
| 2004/0244802 A1 | 12/2004 | Tanaka |
| 2004/0244803 A1 | 12/2004 | Tanaka |
| 2005/0005936 A1 | 1/2005 | Wondka |
| 2005/0015106 A1 | 1/2005 | Perkins et al. |
| 2005/0022809 A1 | 2/2005 | Wondka |
| 2005/0025816 A1 | 2/2005 | Tanaka |
| 2005/0033310 A1 | 2/2005 | Alferness et al. |
| 2005/0033344 A1 | 2/2005 | Dillard et al. |
| 2005/0043745 A1 | 2/2005 | Alferness et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0066976 A1 | 3/2005 | Wondka |
| 2005/0085801 A1 | 4/2005 | Cooper et al. |
| 2005/0096529 A1 | 5/2005 | Cooper et al. |
| 2005/0103340 A1 | 5/2005 | Wondka |
| 2005/0107783 A1 | 5/2005 | Tom et al. |
| 2005/0131276 A1 | 6/2005 | Alferness et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0161040 A1 | 7/2005 | Tanaka |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178385 A1 | 8/2005 | Dellaca' et al. |
| 2005/0178389 A1 | 8/2005 | Shaw et al. |
| 2005/0192526 A1 | 9/2005 | Biggs et al. |
| 2005/0203483 A1 | 9/2005 | Perkins et al. |
| 2005/0205097 A1 | 9/2005 | Kyle, Jr. |
| 2005/0244401 A1 | 11/2005 | Ingenito |
| 2005/0281797 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |

| | | | |
|---|---|---|---|
| 2006/0025815 A1 | 2/2006 | McGurk et al. | |
| 2006/0047291 A1 | 3/2006 | Barry | |
| 2006/0076023 A1 | 4/2006 | Rapacki et al. | |
| 2006/0079838 A1 | 4/2006 | Walker et al. | |
| 2006/0095002 A1 | 5/2006 | Soltesz et al. | |
| 2006/0107961 A1 | 5/2006 | Tanaka | |
| 2006/0116749 A1 | 6/2006 | Willink et al. | |
| 2006/0118125 A1 | 6/2006 | Tanaka | |
| 2006/0118126 A1 | 6/2006 | Tanaka | |
| 2006/0124126 A1* | 6/2006 | Tanaka | 128/200.26 |
| 2006/0130830 A1 | 6/2006 | Barry | |
| 2006/0135947 A1 | 6/2006 | Soltesz et al. | |
| 2006/0135984 A1 | 6/2006 | Kramer et al. | |
| 2006/0142672 A1 | 6/2006 | Keast et al. | |
| 2006/0161233 A1 | 7/2006 | Barry et al. | |
| 2006/0162731 A1 | 7/2006 | Wondka et al. | |
| 2006/0206147 A1 | 9/2006 | DeVore et al. | |
| 2006/0212046 A1 | 9/2006 | Pearce et al. | |
| 2006/0212051 A1 | 9/2006 | Snyder et al. | |
| 2006/0235432 A1 | 10/2006 | DeVore et al. | |
| 2006/0235467 A1 | 10/2006 | DeVore | |
| 2006/0264772 A1 | 11/2006 | Aljuri et al. | |
| 2006/0276807 A1 | 12/2006 | Keast et al. | |
| 2006/0280772 A1 | 12/2006 | Roschak et al. | |
| 2006/0280773 A1 | 12/2006 | Roschak et al. | |
| 2006/0283462 A1 | 12/2006 | Fields et al. | |
| 2007/0005083 A1 | 1/2007 | Sabanathan et al. | |
| 2007/0027434 A1 | 2/2007 | Pedersen et al. | |
| 2007/0043350 A1 | 2/2007 | Soltesz et al. | |
| 2007/0051372 A1 | 3/2007 | Tanaka | |
| 2007/0055175 A1 | 3/2007 | Caro | |
| 2007/0088300 A1 | 4/2007 | Cline et al. | |
| 2007/0123922 A1 | 5/2007 | Cooper et al. | |
| 2007/0128174 A1 | 6/2007 | Kleinsek et al. | |
| 2007/0142742 A1 | 6/2007 | Aljuri et al. | |
| 2007/0163598 A1 | 7/2007 | Chang et al. | |
| 2007/0185531 A1 | 8/2007 | Rimbaugh et al. | |
| 2007/0186932 A1 | 8/2007 | Wondka et al. | |
| 2007/0186933 A1 | 8/2007 | Domingo et al. | |
| 2007/0299424 A1 | 12/2007 | Cumming et al. | |
| 2008/0281151 A1 | 11/2008 | Chang et al. | |
| 2008/0281295 A1 | 11/2008 | Chang et al. | |
| 2008/0281433 A1 | 11/2008 | Chang et al. | |
| 2008/0283065 A1 | 11/2008 | Chang et al. | |
| 2008/0287878 A1 | 11/2008 | Tanaka | |
| 2008/0287973 A1 | 11/2008 | Aster et al. | |
| 2008/0295829 A1 | 12/2008 | Evens | |
| 2009/0205641 A1 | 8/2009 | Tanaka | |
| 2009/0205643 A1 | 8/2009 | Tanaka et al. | |
| 2009/0205644 A1 | 8/2009 | Tanaka et al. | |
| 2009/0205645 A1 | 8/2009 | Tanaka et al. | |
| 2009/0205646 A1 | 8/2009 | Tanaka et al. | |
| 2009/0205647 A1 | 8/2009 | Plough et al. | |
| 2009/0205648 A1 | 8/2009 | Tanaka et al. | |
| 2009/0205649 A1 | 8/2009 | Tanaka et al. | |
| 2009/0205650 A1 | 8/2009 | Tanaka et al. | |
| 2009/0205651 A1 | 8/2009 | Tanaka et al. | |
| 2009/0205658 A1 | 8/2009 | Tanaka et al. | |
| 2009/0205665 A1 | 8/2009 | Tanaka et al. | |
| 2009/0209856 A1 | 8/2009 | Tanaka et al. | |
| 2009/0209906 A1 | 8/2009 | Tanaka et al. | |
| 2009/0209909 A1 | 8/2009 | Tanaka et al. | |
| 2009/0209917 A1 | 8/2009 | Tanaka et al. | |
| 2009/0209924 A1 | 8/2009 | Tanaka | |
| 2009/0209936 A1 | 8/2009 | Tanaka et al. | |
| 2009/0209970 A1 | 8/2009 | Tanaka et al. | |
| 2009/0209971 A1 | 8/2009 | Tanaka et al. | |

FOREIGN PATENT DOCUMENTS

| | | |
|---|---|---|
| EP | 1658867 | 5/2006 |
| EP | 1815821 | 8/2007 |
| EP | 2242527 | 10/2010 |
| JP | 62-2028747 U | 6/1986 |
| JP | 2000197706 | 7/2000 |
| RU | 2192185 | 10/2002 |
| WO | WO 96/39960 | 12/1996 |
| WO | WO 99/66975 | 12/1999 |
| WO | WO 00/76577 A1 | 12/2000 |
| WO | WO 01/45568 A1 | 6/2001 |
| WO | WO2005070480 | 8/2005 |

OTHER PUBLICATIONS

Extended European Search Report dated Jun. 15, 2011 for PCT/US2009034322, 7 pages.

Extended European Search Report dated Sep. 16, 2011 for PCT/US2009034380, 8 pages.

Rendina et al., "Feasibility and safety of the airway bypass procedure for patients with emphysema", The Journal of Thoracic and Cardiovascular Surgery 2003; 125: 1294-1299.

Rockey, Edward E., "Tube Pneumonostomy for Thoracotomy Reject Crippling Bulbous Emphysema", New York State Journal of Medicine Mar. 1, 1973: 664-671.

Rousseau et al., "Self-expandable Prostheses in the Tracheobronchial Tree", Thoracic Radiology 1993; 188: 199-203.

Russi et al., "Lung volume reduction surgery: what can we learn from the National Emphysema Treatment Trial?" European Respiratory Journal 2003; 22: 571-573.

Saad et al., "Surgical treatment of bullae for Bulbous emphysema: a simple drainage", J. Pneumologia 2000; 26(3): 1-11, retrieved from <http://www.scielo.br/scielo.php?script=arttext&pid=S0102-35862000000300003&lng=e . . . > May 2, 2007.

Shah, Pallav, "Surgical and Non-surgical Volume Reduction for COPD", Presented at the Clinical Consensus on COPD, Mar. 2-3, 2007, Novotel London West, pp. 1-44.

Shah et al., "Surgical Treatment of Bulbous Emphysema: Experience with the Brompton Technique", Annals of Thoracic Surgery 1994; 58: 1452-1456.

Shim et al., "Percutaneous Drainage of Lung Abscess", Lung 1990; 168: 201-207.

Snell et al., "The Potential for Bronchoscopic Lung Volume Reduction Using Bronchial Prostheses: A Pilot Study", Chest 2003; 124: 1073-1080.

Snell, Gregory I., "Airway Bypass Stenting for Severe Emphysema", retrieved from <http://www.ctsnet.org/sections/thoracic/newtechnology/article-4.html>, Aug. 6, 2007, 4 pages.

Springmeyer, Steven C., "Development of a Bronchial Valve for Treatment of Severe Emphysema", retrieved from <http://www.ctsnet.org/sections/thoracic/newtechnology/article-10.html>, Jul. 16, 2007, 6 pages.

Stewart et al., "Decompression of Giant Bulla in Acute Pneumonia: Surgical Palliation Prior to Definitive Management", Ann Thoracic Surg 2006; 82: 2308-2309.

Sugarmann et al., "Mesh insertion as an aid for pleurodesis", Journal of Cardiovascular Surgery 1996; 37 (Suppl. 1 to No. 6):173-5.

Swallow et al., "Quadriceps strength predicts mortality in patients with moderate to severe chronic obstructive pulmonary disease", Thorax 2007; 62: 115-120.

Symbas et al., "Nontuberculous Pleural Empyema in Adults, The Role of a Modified Eloesser Procedure in Its Management", The Annals of Thoracic Surgery 1971; 12: 69-78.

Takizawa et al., "Computed tomography-guided drainage for large pulmonary bullae", Interactive Cardiovascular and Thoracic Surgery 2004; 3: 283-285.

Terry et al., "Collateral Ventilation in Man", The New England Journal of Medicine 1978; 298(1): 10-15.

Thourani et al., "Twenty-six Years of Experience With the Modified Eloesser Flap", Ann Thorac Surg 2003; 76: 401-406.

Toma et al., "Brave new world for interventional bronchoscopy", Thorax 2005; 60: 180-181.

Ugama et al., "Drainage of Giant Bulla with Balloon Catheter Using Chemical Irritant and Fibrin Glue", Chest 1988; 94(6): 1289-1290.

Vainrub et al., "Percutaneous Drainage of Lung Abscess", American Review of Respiratory Disease 1978; 117: 153-160.

Venn et al., "Intracavity drainage for Bulbous, emphysematous lung disease: experience with the Brompton technique", Thorax 1988; 43: 998-1002.

Wood et al., "A multicenter trial of an intrabronchial valve for treatment of severe emphysema", The Journal of Thoracic and Cardiovascular Surgery 2007; 133: 65-73.e2.

Woodring et al., "Pneumothorax ex vacuo", Chest 1996, 110: 1102-1124.

Woolcock et al., "Mechanical factors influencing collateral ventilation in human, dog, and pig lungs", Journal of Applied Physiology 1971, 30: 99-115.

Yellin et al., "Percutaneous Tube Drainage: The Treatment of Choice for Refractory Lung Abscess", The Annals of Thoracic Surgery 1985; 39: 266-270.

Yim et al., "Minimally invasive thoracic surgery: where do we stand now?" Hong Kong Medical Journal 1995; 1: 115-122.

Yim et al., "Early results of endoscopic lung volume reduction for emphysema", The Journal of Thoracic and Cardiovascular Surgery 2004; 127: 1564-1573.

International Search Report for PCT/US/2009/034374 dated Aug. 28, 2009; 13 pages.

International Search Report for PCT/US/2009/034380 dated Sep. 24, 2009; 12 pages.

International Search Report for PCT/US2009/034322 dated Oct. 5, 2009; 14 pages.

International Search Report for PCT/US2009/034406 dated Dec. 2, 2009; 16 pages.

Aljuri et al., "Validation and pilot clinical study of a new bronchoscopic method to measure collateral ventilation before endobronchial lung volume reduction", J Appl Physio 106: 774-783, 2009.

Al-Salem et al., "Computed tomography-guided percutaneous needle aspiration of lung abscesses in neonates and children", Pediatr Surg Int (1997) 12: 417-419, copyright Springer-Verlag 1997.

Ball, JR et al., "Percutaneous Drainage of Chest Abscesses in Children", Radiology 1989; 171: 431-434.

Becker et al., "Lung Volumes before and after Lung Volume Reduction Surgery: Quantitative CT Analysis", Am J Respir Crit Care Med 1998; 157: 1593-1599.

Brenner et al., "Innovative Approaches to Lung Volume Reduction for Emphysema", Chest 2004; 126: 238-248.

Brutinel et al., "A two-year experience with the neodymium-YAG laser in endobronchial obstruction", Chest 1987; 91: 159-165.

Celli et al. "Standards for the diagnosis and treatment of patients with COPD: a summary of the ATS/ERS position paper", European Respiratory Journal 2004; 23; 932-946.

Cetti et al., "Collateral ventilation", Thorax 2006; 61: 371-373.

Chino et al., "Ventilation of Excised Human Lungs Via Spiracles through the Pleura", Thematic Poster Session (Abstract p. A546) Session: 12:45 pm-4:15 pm, Mechanics of the Lung and Respiratory System, (2003).

Choong et al., "Feasibility and safety of airway bypass stent placement and influence of topical mitomycin C on stent patency", The Journal of Thoracic and Cardiovascular Surgery 2005; 129: 632-638.

Choong et al., "Transpleural ventilation of explanted human lungs", Thorax 2007; 62: 623-630; originally published online Apr. 5, 2007.

Cope, J. Hallam, "Monaldi Procedure", Presented at the annual meeting of the California Tuberculosis and Health Association and the California Trudeau Society, Mar. 30-Apr. 1, 1950, San Diego; retrieved from California Medicine Dec. 1950; vol. 73, No. 6: 563-564.

Dumon, J. F., "A Dedicated Tracheobronchial Stent", Chest 1990; 97: 328-332.

Eloesser, "An Operation for Tuberculous Empyema", Chest 1935; 1: 8-23.

Fein, Alan M, "Lung Volume Reduction Surgery: Answering the Crucial Questions", Chest 1998; 113: 277-282.

Fernandes et al., "*Airway Hyperresponsiveness: From Molecules to Bedside Invited Review*: Do inflammatory mediators influence the contribution of airway smooth muscle contraction to airway hyperresponsiveness in asthma?", Journal Appl Physiol 2003; 95; 844-853.

Fessler, Henry E., "Collateral Ventilation, the Bane of Bronchoscopic Volume Reduction", Am J Respir Crit Care Med 2005; 171: 423-425.

Frawley et al., "Airway Pressure Release Ventilation: Theory and Practice", AACN Clinical Issues 2001; vol. 12, No. 2: 234-246.

Freitag et al., "Theoretical and experimental basis for the development of a dynamic airway stent", European Respiratory Journal 1994; 7: 2038-2045.

Ghaye et al., "Imaging guided thoracic interventions", European Respiratory Journal 2001; 17: 507-528.

Golding et al., "External drainage of large bullae in severe generalized emphysema", Journal of Thoracic and Cardiovascular Surgery Jun. 1968; vol. 55, No. 6: 891-894.

Goldstraw et al., "The Surgical Treatment of Emphysema: The Brompton Approach", Chest Surgery Clinics of North America Nov. 1995; vol. 5, No. 4: 777-797.

Habashi, Nader M., "Other approaches to open-lung ventilation: Airway pressure release ventilation", Crit Care Med 2005, vol. 33, No. 3 (Suppl): S228-S240.

Harada et al., "Re-expansion of Refractory Atelectasis Using a Bronchofiberscope with a Balloon Cuff", Chest 1983; 84: 725-728.

Head et al., "Intracavitary Suction (Monaldi) in the Treatment of Emphysematous Bullae and Blebs", Journal of Thoracic Surgery Dec. 1949; vol. 18, No. 6: 761-776.

Heimlich, Henry J., "Respiratory Rehabilitation with Transtracheal Oxygen System", Ann Otol Rhinol Laryngol Nov./Dec. 1982; 91: 643-647.

Hogg et al., "Chronic obstructive pulmonary disease c2: Pathology and biochemistry of emphysema", Thorax 2002; 57: 830-834.

Hogg et al., "The Resistance of Collateral Channels in Excised Human Lungs", Journal of Clinical Investigation 1969; 48: 421-431.

Joannette, Albert, "Drainage of Tuberculous Cavities by Aspiration (Monaldi Method)", The Canadian Medical Association Journal Jan. 1941; 46-48.

Korpela et al., "Bioabsorbable Self-reinforced Poly-L-Lactide, Metallic, and Silicone Stents in the Management of Experimental Tracheal Stenosis", Chest 1999; 115: 490-495.

Lausberg et al., "Bronchial Fenestration Improves Expiratory Flow in Emphysematous Human Lungs", Annals of Thoracic Surgery 2003; 75: 393-398.

Lorenzo et al., "Lung Abscesses in Children: Diagnostic and Therapeutic Needle Aspiration", Radiology Oct. 1985; 157: 79-80.

MacArthur et al., "Intracavity suction and drainage in the treatment of emphysematous bullae", Thorax 1977; 32: 668-672.

MacKlem, Peter T., "Collateral Ventilation", The New England Journal of Medicine Jan. 5, 1978; 298(1): 49-50.

Matson et al., "Evaluation of Various Surgical Procedures in the Treatment of Pulmonary Tuberculosis", Chest 1946; 12: 40-47.

McCoy, Robert, "Oxygen-Conserving Techniques and Devices", Respiratory Care Jan. 2000, vol. 45, No. 1: 95-104.

Meyers et al., "Chronic obstructive pulmonary disease 10: Bullectomy, lung volume reduction surgery, and transplantation for patients with chronic obstructive pulmonary disease", Thorax 2003; 58: 634-638.

Mineo et al., "Awake Nonresectional Lung Volume Reduction Surgery", Annals of Surgery 2006; 243: 131-136.

Monaldi, V., "Endocavitary Aspiration: Its Practical Application", Tubercle 1947: 223-228.

Monaldi, V., "Endocavitary Aspiration in the Treatment of Lung Abscess", Chest 1956; 29: 193-201.

Monaldi, V., "Endocavitary Aspiration in the Treatment of Pathological Cavities of the Lung", Proceedings of the International Conference on Tuberculosis, Scandinavian Journal of Respiratory Diseases Supplementum 1968; 65: 113-121.

U.S. Department of Health and Human Services; National Institutes of Health National Heart, Lung, and Blood Institute; "Chronic Obstructive Pulmonary Disease", NIH Publication No. 03-5229 Mar. 2003: 1-6.

Parker et al., "Percutaneous small bore catheter drainage in the management of lung abscesses", Chest 1987; 92: 213-218.

Petty, Thomas L., "The history of COPD", International Journal of COPD 2006; 1(1): 3-14.

Polkey, M. J., "Surgical procedures in emphysema: any impact on dynamic hyperinflation?" European Respiratory Review 2006; 15(100): 96-98.

Polkey, M. J., "Bronchoscopic lung volume reduction", European Respiratory Review 2006; 15(100): 99-103.

* cited by examiner

PNEUMOSTOMA MANAGEMENT SYSTEM HAVING A COSMETIC AND/OR PROTECTIVE COVER

CLAIM TO PRIORITY

This application claims priority to all of the following applications including: U.S. Provisional Application No. 61/029,830, filed Feb. 19, 2008, entitled "ENHANCED PNEUMOSTOMA MANAGEMENT DEVICE AND METHODS FOR TREATMENT OF CHRONIC OBSTRUCTIVE PULMONARY DISEASE";

U.S. Provisional Application No. 61/032,877, filed Feb. 29, 2008, entitled "PNEUMOSTOMA MANAGEMENT SYSTEM AND METHODS FOR TREATMENT OF CHRONIC OBSTRUCTIVE PULMONARY DISEASE";

U.S. Provisional Application No. 61/038,371, filed Mar. 20, 2008, entitled "SURGICAL PROCEDURE AND INSTRUMENT TO CREATE A PNEUMOSTOMA AND TREAT CHRONIC OBSTRUCTIVE PULMONARY DISEASE";

U.S. Provisional Application No. 61/082,892, filed Jul. 23, 2008, entitled "PNEUMOSTOMA MANAGEMENT SYSTEM HAVING A COSMETIC AND/OR PROTECTIVE COVER";

U.S. Provisional Application No. 61/083,573, filed Jul. 25, 2008, entitled "DEVICES AND METHODS FOR DELIVERY OF A THERAPEUTIC AGENT THROUGH A PNEUMOSTOMA";

U.S. Provisional Application No. 61/084,559, filed Jul. 29, 2008, entitled "ASPIRATOR FOR PNEUMOSTOMA MANAGEMENT";

U.S. Provisional Application No. 61/088,118, filed Aug. 12, 2008, entitled "FLEXIBLE PNEUMOSTOMA MANAGEMENT SYSTEM AND METHODS FOR TREATMENT OF CHRONIC OBSTRUCTIVE PULMONARY DISEASE";

U.S. Provisional Application No. 61/143,298, filed Jan. 8, 2009, entitled "METHODS AND APPARATUS FOR THE CRYOTHERAPY CREATION OR RE-CREATION OF PNEUMOSTOMY"; and U.S. Provisional Application No. 61/151,581, filed Feb. 11, 2009, entitled "SURGICAL INSTRUMENTS AND PROCEDURES TO CREATE A PNEUMOSTOMA AND TREAT CHRONIC OBSTRUCTIVE PULMONARY DISEASE".

All of the afore-mentioned applications are incorporated herein by reference in their entireties.

CROSS-REFERENCE TO RELATED APPLICATIONS

This application is related to all of the above provisional applications and all the patent applications that claim priority thereto including:

This application is related to all of the following applications including U.S. patent application Ser. No. 12/388,465, filed Feb. 18, 2009, now U.S. Pat. No. 7,909,803, issued Mar. 22, 2011, entitled "ENHANCED PNEUMOSTOMA MANAGEMENT DEVICE AND METHODS FOR TREATMENT OF CHRONIC OBSTRUCTIVE PULMONARY DISEASE";

U.S. patent application Ser. No. 12/388,447, filed Feb. 18, 2009, entitled "PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,451, filed Feb. 18, 2009, entitled "PNEUMOSTOMA MANAGEMENT METHOD FOR TREATMENT OF CHRONIC OBSTRUCTIVE PULMONARY DISEASE";

U.S. patent application Ser. No. 12/388,435, filed Feb. 18, 2009, entitled "TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,438, filed Feb. 18, 2009, entitled "ACCELERATED TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,441, filed Feb. 18, 2009, entitled "SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,446, filed Feb. 18, 2009, entitled "PERCUTANEOUS SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,455, filed Feb. 18, 2009, entitled "DEVICES AND METHODS FOR DELIVERY OF A THERAPEUTIC AGENT THROUGH A PNEUMOSTOMA";

U.S. patent application Ser. No. 12/388,461, filed Feb. 18, 2009, now U.S. Pat. No. 8,348,906, issued Jan. 8, 2013, entitled "ASPIRATOR FOR PNEUMOSTOMA MANAGEMENT";

U.S. patent application Ser. No. 12/388,462, filed Feb. 18, 2009, now U.S. Pat. No. 7,927,324, issued Apr. 19, 2011, entitled "ASPIRATOR AND METHOD FOR PNEUMOSTOMA MANAGEMENT";

U.S. patent application Ser. No. 12/388,458, filed Feb. 18, 2009, entitled "FLEXIBLE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,459, filed Feb. 18, 2009, entitled "METHODS AND DEVICES FOR FOLLOW-UP CARE AND TREATMENT OF A PNEUMOSTOMA";

U.S. patent application Ser. No. 12/388,453, filed Feb. 18, 2009, now U.S. Pat. No. 8,252,003 issued Aug. 28, 2012, entitled "SURGICAL INSTRUMENTS FOR CREATING A PNEUMOSTOMA AND TREATING CHRONIC OBSTRUCTIVE PULMONARY DISEASE";

U.S. patent application Ser. No. 12/388,466, filed Feb. 18, 2009, entitled "ONE-PIECE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,467, filed Feb. 18, 2009, now U.S. Pat. No. 8,347,880 issued Jan. 8, 2013, entitled "PNEUMOSTOMA MANAGEMENT SYSTEM WITH SECRETION MANAGEMENT FEATURES FOR TREATMENT OF CHRONIC OBSTRUCTIVE PULMONARY DISEASE";

U.S. patent application Ser. No. 12/388,468, filed Feb. 18, 2009, now U.S. Pat. No. 8,365,722 issued Feb. 5, 2013, entitled "MULTI-LAYER PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,469, filed Feb. 18, 2009, entitled "VARIABLE LENGTH PNEUMOSTOMA MANAGEMENT SYSTEM FOR TREATMENT OF CHRONIC OBSTRUCTIVE PULMONARY DISEASE"; and U.S. patent application Ser. No. 12/388,470, filed Feb. 18, 2009, now U.S. Pat. No. 8,021,320 issued Sep. 20, 2011, entitled "SELF-SEALING DEVICE AND METHOD FOR DELIVERY OF A THERAPEUTIC AGENT THROUGH A PNEUMOSTOMA".

All of the afore-mentioned applications are incorporated herein by reference in their entireties. This patent application also incorporates by reference all patents, applications, and articles discussed and/or cited herein.

BACKGROUND OF THE INVENTION

In the United States alone, approximately 14 million people suffer from some form of Chronic Obstructive Pulmonary Disease (COPD). However an additional ten million adults have evidence of impaired lung function indicating that COPD may be significantly underdiagnosed. The cost of COPD to the nation in 2002 was estimated to be $32.1 billion. Medicare expenses for COPD beneficiaries were nearly 2.5 times that of the expenditures for all other patients. Direct medical services accounted for $18.0 billion, and indirect cost of morbidity and premature mortality was $14.1 billion. COPD is the fourth leading cause of death in the U.S. and is projected to be the third leading cause of death for both males and females by the year 2020.

Chronic Obstructive Pulmonary Disease (COPD) is a progressive disease of the airways that is characterized by a gradual loss of lung function. In the United States, the term COPD includes chronic bronchitis, chronic obstructive bronchitis, and emphysema, or combinations of these conditions. In emphysema the alveoli walls of the lung tissue are progressively weakened and lose their elastic recoil. The breakdown of lung tissue causes progressive loss of elastic recoil and the loss of radial support of the airways which traps residual air in the lung. This increases the work of exhaling and leads to hyperinflation of the lung. When the lungs become hyperinflated, forced expiration cannot reduce the residual volume of the lungs because the force exerted to empty the lungs collapses the small airways and blocks air from being exhaled. As the disease progresses, the inspiratory capacity and air exchange surface area of the lungs is reduced until air exchange becomes seriously impaired and the individual can only take short shallow labored breaths (dyspnea).

The symptoms of COPD can range from the chronic cough and sputum production of chronic bronchitis to the severe disabling shortness of breath of emphysema. In some individuals, chronic cough and sputum production are the first signs that they are at risk for developing the airflow obstruction and shortness of breath characteristic of COPD. With continued exposure to cigarettes or noxious particles, the disease progresses and individuals with COPD increasingly lose their ability to breathe. Acute infections or certain weather conditions may temporarily worsen symptoms (exacerbations), occasionally where hospitalization may be required. In others, shortness of breath may be the first indication of the disease. The diagnosis of COPD is confirmed by the presence of airway obstruction on testing with spirometry. Ultimately, severe emphysema may lead to severe dyspnea, severe limitation of daily activities, illness and death.

There is no cure for COPD or pulmonary emphysema, only various treatments, for ameliorating the symptoms. The goal of current treatments is to help people live with the disease more comfortably and to prevent the progression of the disease. The current options include: self-care (e.g., quitting smoking), medications (such as bronchodilators which do not address emphysema physiology), long-term oxygen therapy, and surgery (lung transplantation and lung volume reduction surgery). Lung Volume Reduction Surgery (LVRS) is an invasive procedure primarily for patients who have a localized (heterogeneous) version of emphysema; in which, the most diseased area of the lung is surgically removed to allow the remaining tissue to work more efficiently. Patients with diffuse emphysema cannot be treated with LVRS, and typically only have lung transplantation as an end-stage option. However, many patients are not candidates for such a taxing procedure.

A number of less-invasive surgical methods have been proposed for ameliorating the symptoms of COPD. In one approach new windows are opened inside the lung to allow air to more easily escape from the diseased tissue into the natural airways. These windows are kept open with permanently implanted stents. Other approaches attempt to seal off and shrink portions of the hyperinflated lung using chemical treatments and/or implantable plugs. However, these proposals remain significantly invasive and are still in clinical trails. None of the surgical approaches to treatment of COPD has been widely adopted. Therefore, a large unmet need remains for a medical procedure that can sufficiently alleviate the debilitating effects of COPD and emphysema and is accepted by physicians and patients.

SUMMARY OF THE INVENTION

In view of the disadvantages of the state of the art, Applicants have developed a method for treating COPD in which an artificial passageway is made through the chest wall into the lung. An anastomosis is formed between the artificial passageway and the lung by creating a pleurodesis between the visceral and parietal membranes surrounding the passageway as it enters the lung. The pleurodesis prevents air from entering the pleural cavity and causing a pneumothorax (deflation of the lung due to air pressure in the pleural cavity). The pleurodesis is stabilized by a fibrotic healing response between the membranes. The artificial passageway through the chest wall also becomes epithelialized. The result is a stable artificial aperture through the chest wall which communicates with the parenchymal tissue of the lung.

The stable artificial aperture into the lung through the chest is referred to herein as a pneumostoma. A pneumostoma provides an extra pathway that allows air to exit the lung while bypassing the natural airways which have been impaired by COPD and emphysema. By providing this ventilation bypass, the pneumostoma allows the stale air trapped in the lung to escape from the lung thereby shrinking the lung (reducing hyperinflation). By shrinking the lung, the ventilation bypass reduces breathing effort (reducing dyspnea), allows more fresh air to be drawn in through the natural airways and increases the effectiveness of all of the tissues of the lung for gas exchange. Increasing the effectiveness of gas exchange allows for increased absorption of oxygen into the bloodstream and also increased removal of carbon dioxide. Reducing the amount of carbon dioxide retained in the lung reduces hypercapnia which also reduces dyspnea. The pneumostoma thereby achieves the advantages of lung volume reduction surgery without surgically removing a portion of the lung or sealing off a portion of the lung.

A patient is typically provided with a pneumostoma management system to protect the pneumostoma and keep the pneumostoma open on a day-to-day basis. In general terms, a pneumostoma management device ("PMD") comprises a tube which is inserted into the pneumostoma and an external component which is secured to the skin of the patient to keep the tube in place. Gases escape from the lung through the tube and are vented external to the patient. The pneumostoma management device may, in some, but not all cases, include a filter which only permits gases to enter or exit the tube. The pneumostoma management device may, in some, but not all cases, include a one-way valve which allows gases to exit the lung but not enter the lung through the tube. Additional details and variations of pneumostoma management devices are described in applicants' pending and issued patents and applications including those patent applications incorporated by reference above.

A pneumostoma management system in accordance with embodiments of the present invention is desirable to promote patient observance of a regimen to maintain the patency of the pneumostoma and control flow of materials between the exterior of the patient and the parenchymal tissue of the lung via a pneumostoma.

In accordance with a general embodiment, the present invention comprises a pneumostoma management system including a pneumostoma management device and a removable protective and/or cosmetic cover.

In accordance with one embodiment, the present invention provides a pneumostoma management system which includes a partially-implantable pneumostoma vent, a chest mount and a removable cover. The cover attaches to the pneumostoma management device to control the exterior profile and/or appearance of the pneumostoma management device.

In accordance with one embodiment, the present invention provides a pneumostoma management system comprising a cover and a pneumostoma management device. The pneumostoma management device comprises a tube for insertion in a pneumostoma connected to an external section for securing the pneumostoma management device to the chest of a patient. The cover is configured to attach to the pneumostoma management device such that it presents an outward surface which substantially obscures the external section of the pneumostoma management device from view. The outward surface of the cover is designed to have a preferred visual appearance compared to the external section of the pneumostoma management device.

In accordance with one embodiment the present invention provided, a pneumostoma management system which includes a pneumostoma management device and a cover. The pneumostoma management device maintains the patency of a pneumostoma while controlling the flow of material through the pneumostoma. The pneumostoma management device includes a hydrophobic filter and/or a one-way filter. The cover serves to protect the pneumostoma management device and/or provide a cosmetic skin to make the pneumostoma management device more acceptable to the patient and thereby encourage patient compliance with a pneumostoma treatment regimen.

In accordance with one embodiment, the present invention provides pneumostoma management system which includes a partially-implantable pneumostoma management device which can be placed into a pneumostoma to prevent the entry of foreign substances into the lung, control air flow through the pneumostoma and collect any materials that may exit the lung and a removable cover which attaches to the pneumostoma management device to control the exterior profile and/or appearance of the pneumostoma management device.

In accordance with one embodiment, the present invention provides a pneumostoma management system which includes a partially-implantable pneumostoma vent, a chest mount and a cover. The partially-implantable pneumostoma vent is placed into a pneumostoma through an aperture in the chest mount. The chest mount is secured to the skin of the patient and is replaced every two days to one week. The pneumostoma vent is replaced daily or when necessary. The cover is reusable.

Thus, various systems, components and methods are provided for managing a pneumostoma and thereby treating COPD. Other objects, features and advantages of the invention will be apparent from drawings and detailed description to follow.

BRIEF DESCRIPTION OF THE DRAWINGS

The above and further features, advantages and benefits of the present invention will be apparent upon consideration of the present description taken in conjunction with the accompanying drawings.

DETAILED DESCRIPTION OF THE INVENTION

Figure 1A:
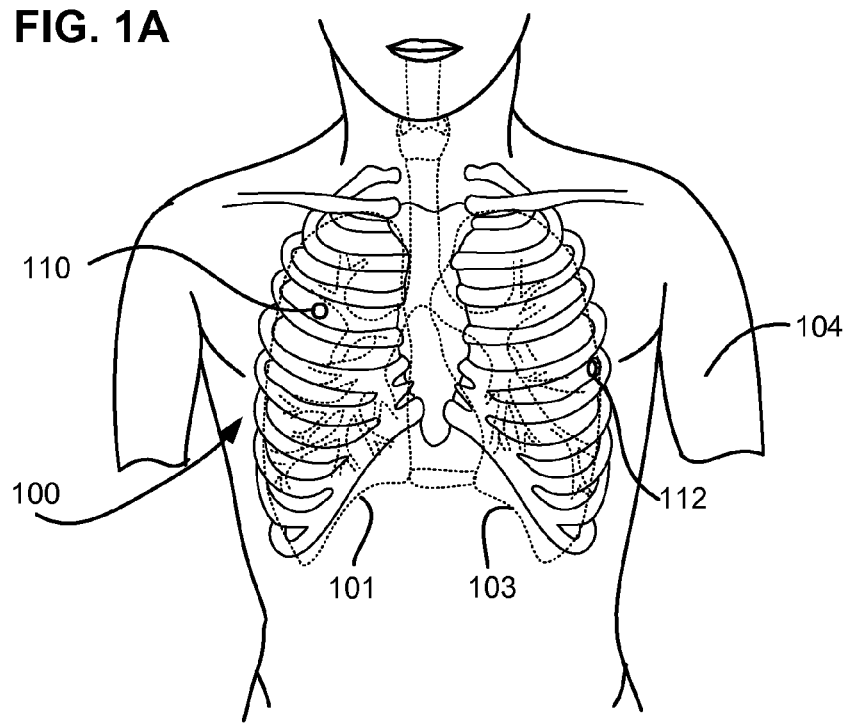
FIG. 1A shows the chest of a patient indicating alternative locations for a pneumostoma that may be managed using the device and methods of the present invention.

The present invention provides in some embodiments a pneumostoma management system which includes a pneumostoma management device for maintaining the patency of a pneumostoma and cover. The pneumostoma management device includes a hydrophobic filter and/or a one-way filter. The cover serves to protect the pneumostoma management device and/or provide a cosmetic skin to make the pneumostoma management device more acceptable to the patient and thereby encourage patient compliance with a pneumostoma treatment regimen.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

Pneumostoma Formation and Anatomy

FIG. 1A shows the chest of a patient identifying alternative locations for creating a pneumostoma that may be managed using the system of the present invention. A first pneumostoma 110 is shown on the front of the chest 100 over the right lung 101 (shown in dashed lines). The pneumostoma is preferably positioned over the third intercostal space on the midclavicular line. Thus, the pneumostoma 110 is located on the front of the chest between the third and fourth ribs. Although the pneumostoma 110 is preferably located between two ribs, in alternative procedures a pneumostoma can also be prepared using a minithoracotomy with a rib resection.

In FIG. 1A, a second pneumostoma 112 is illustrated in a lateral position entering the left lung 103 (shown in dashed lines). The pneumostoma 112 is preferably positioned over the fourth or fifth intercostal space under the left arm 104. In general, one pneumostoma per lung is created; however, more or less than one pneumostoma per lung may be created depending upon the needs of the patient. In most humans, the lobes of the lung are not completely separate and air may pass between the lobes.

A pneumostoma is surgically created by forming an artificial channel through the chest wall and joining that channel with an opening through the visceral membrane of the lung into parenchymal tissue of the lung to form an anastomosis. The anastomosis is joined and sealed by sealing the channel from the pleural cavity using adhesives, mechanical sealing and/or pleurodesis. Methods for forming the channel, opening, anastomosis and pleurodesis are disclosed in applicants' pending and issued patents and applications including U.S. patent application Ser. No. 10/881,408, now U.S. Pat. No. 7,682,332, entitled "Methods to Accelerate Wound Healing in Thoracic Anastomosis Applications" and U.S. patent application Ser. No. 12/030,006, now U.S. Pat. No. 8,062,315, entitled "Variable Parietal/Visceral Pleural Coupling" which are incorporated herein by reference in their entireties.

Figure 1B:
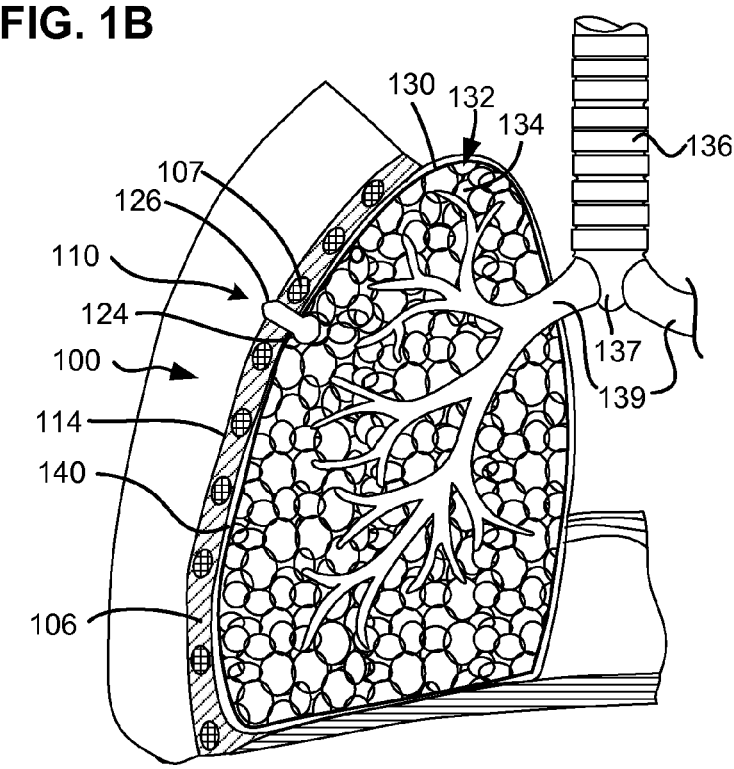
FIG. 1B shows a sectional view of the chest illustrating the relationship between the pneumostoma, lung and natural airways.

FIG. 1B shows a sectional view of chest 100 illustrating the position of the pneumostoma 110. The parenchymal tissue 132 of the lung 130 is comprised principally of alveoli 134. The alveoli 134 are the thin walled air-filled sacs in which gas exchange takes place. Air flows into the lungs through the natural airways including the trachea 136, carina 137, and bronchi 139. Inside the lungs, the bronchi branch into a multiplicity of smaller vessels referred to as bronchioles (not shown). Typically, there are more than one million bronchioles in each lung. Each bronchiole connects a cluster of alveoli to the natural airways. As illustrated in FIG. 1B, pneumostoma 110 comprises a channel through the thoracic wall 106 of the chest 100 between two ribs 107. Pneumostoma 110 opens at an aperture 126 through the skin 114 of chest 100.

Figure 1C:
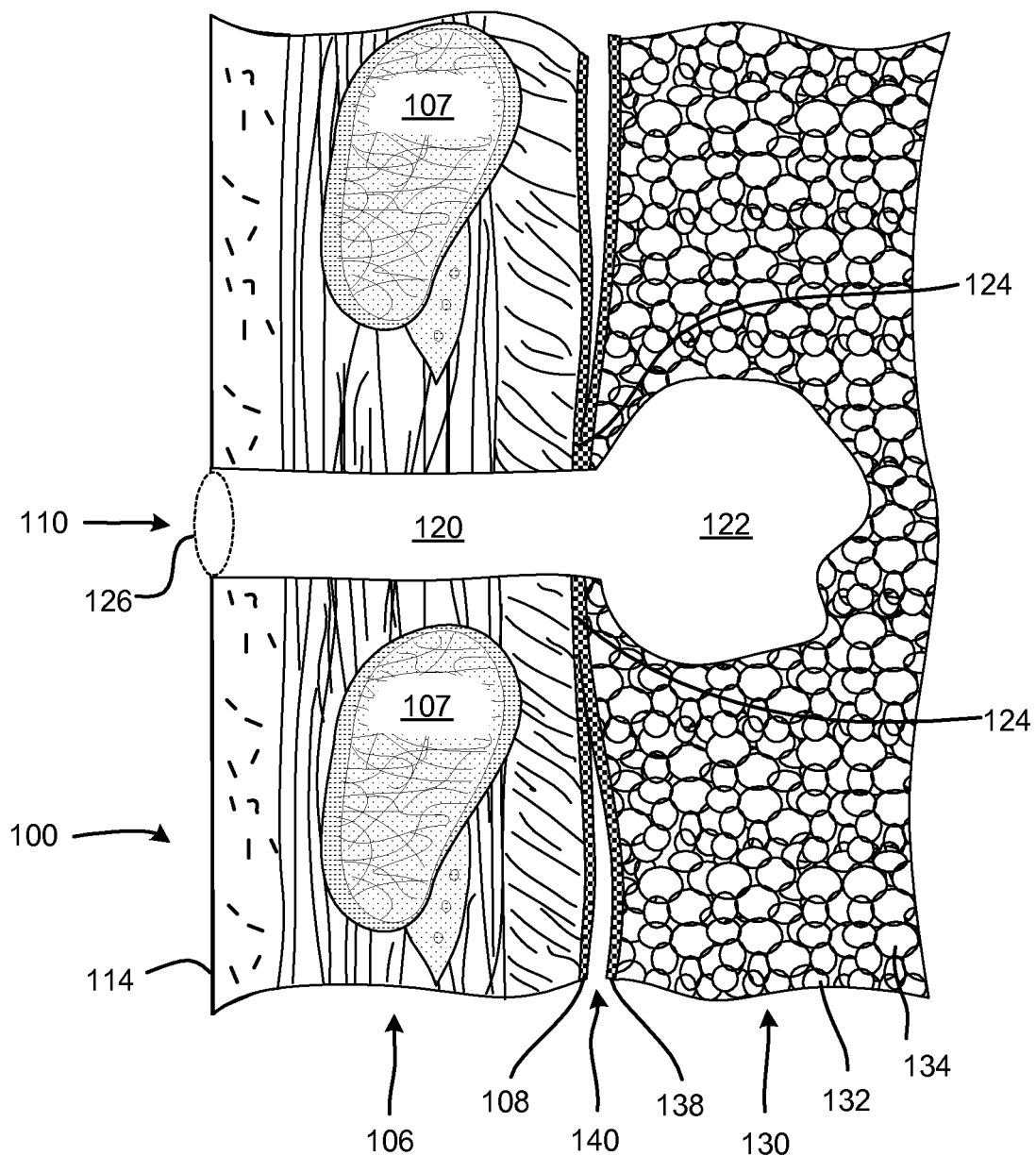
FIG. 1C shows a detailed sectional view of a pneumostoma.

FIG. 1C shows a detailed sectional view of the pneumostoma 110. As illustrated in FIG. 1C, pneumostoma 110 comprises a channel 120 through the thoracic wall 106 of the chest 100 between the ribs 107. The channel 120 is joined to cavity 122 in the parenchymal tissue 132 of lung 130. An adhesion or pleurodesis 124 surrounds the channel 120 where it enters the lung 130. The thoracic wall 106 is lined with the parietal membrane 108. The surface of the lung 130 is covered with a continuous sac called the visceral membrane 138. The parietal membrane 108 and visceral membrane 138 are often referred to collectively as the pleural membranes. Between the parietal membrane 108 and visceral membrane 138 is the pleural cavity (pleural space) 140. The pleural cavity 140 usually only contains a thin film of fluid that serves as a lubricant between the lungs and the chest wall. In pleurodesis 124 the pleural membranes are fused and/or adhered to one another eliminating the space between the pleural membranes in that region.

An important feature of the pneumostoma is the seal or adhesion surrounding the channel 120 where it enters the lung 130 which may comprise a pleurodesis 124. A pleurodesis 124 is the fusion or adhesion of the parietal membrane 108 and visceral membrane 138. A pleurodesis may be a complete pleurodesis in which the entire pleural cavity 140 is removed by fusion of the visceral membrane 138 with the parietal membrane 108 over the entire surface of the lung 130. However, as shown in FIG. 1C, the pleurodesis is preferably localized to the region surrounding the channel 120. The pleurodesis 124 surrounding the channel 120 prevents air from entering the pleural cavity 140. If air is permitted to enter pleural cavity 140, a pneumothorax will result and the lung may collapse.

Pleurodesis 124 can be created between the visceral pleura of the lung and the inner wall of the thoracic cavity using chemical methods including introducing into the pleural space irritants (e.g. iodopovidone or silver nitrate), antibiotics (e.g. Doxycycline or Quinacrine), anticancer drugs (e.g. Bleomycin, Mitoxantrone or Cisplatin), cytokines (e.g. interferon alpha-2β and Transforming growth factor-β); pyrogens (e.g. *Corynebacterium parvum, Staphylococcus aureus* superantigen or OK432); connective tissue proteins (e.g. fibrin or collagen) and minerals (e.g. talc slurry). A pleurodesis can also be created using surgical methods including pleurectomy. For example, the pleural space may be mechanically abraded during thoracoscopy or thoracotomy. This procedure is called dry abrasion pleurodesis. A pleurodesis may also be created using radiotherapy methods, including radioactive gold or external radiation. These methods cause an inflammatory response and/or fibrosis, healing, and fusion of the pleural membranes. Alternatively, a seal can be created in an acute manner between the pleural membranes using biocompatible glues, meshes or mechanical means such as clamps, staples, clips and/or sutures. The adhesive or mechanical seal may develop into pleurodesis over time. A range of biocompatible glues are available that may be used on the lung, including light-activatable glues, fibrin glues, cyanoacrylates and two part polymerizing glues. Applicants' U.S. patent application Ser. No. 12/030,006, now U.S. Pat. No. 8,062,315, entitled "VARIABLE PARIETAL/VISCERAL PLEURAL COUPLING" discloses methods such as pleurodesis for coupling a channel through the chest wall to the inner volume of the lung without causing a pneumothorax and is incorporated herein by reference for all purposes.

When formed, pneumostoma 110 provides an extra pathway for exhaled air to exit the lung 130 reducing residual volume and intra-thoracic pressure without the air passing through the major natural airways such as the bronchi 139 and trachea 136. Collateral ventilation is particularly prevalent in an emphysemous lung because of the deterioration of lung tissue caused by COPD. Collateral ventilation is the term given to leakage of air through the connective tissue between the alveoli 134. Collateral ventilation may include leakage of air through pathways that include the interalveolar pores of Kohn, bronchiole-alveolar communications of Lambert, and interbronchiolar pathways of Martin. This air typically becomes trapped in the lung and contributes to hyperinflation. In lungs that have been damaged by COPD and emphysema, the resistance to flow in collateral channels (not shown) of the parenchymal tissue 132 is reduced allowing collateral ventilation to increase. Air from alveoli 134 of parenchymal tissue 132 that passes into collateral pathways of lung 130 is collected in cavity 122 of pneumostoma 110. Pneumostoma 110, thus, makes use of collateral ventilation to collect air in cavity 122 and vent the air outside the body via channel 120 reducing residual volume and intra-thoracic pressure and bypassing the natural airways which have been impaired by COPD and emphysema.

By providing this ventilation bypass, the pneumostoma allows stale air trapped in the parenchymal tissue 132 to escape from the lung 130. This reduces the residual volume and intra-thoracic pressure. The lower intra-thoracic pressure reduces the dynamic collapse of airways during exhalation. By allowing the airways to remain patent during exhalation, labored breathing (dyspnea) and residual volume (hyperinflation) are both reduced. Pneumostoma 110 not only provides an extra pathway that allows air to exit the lung 130 but also allows more fresh air to be drawn in through the natural airways. This increases the effectiveness of all of the tissues of the lung 130 and improves gas exchange. Pneumostoma 110, thus, achieves many of the advantages sought by lung volume reduction surgery without surgically removing a portion of the lung or sealing off a portion of the lung.

Applicants have found that a pneumostoma management system in accordance with embodiments of the present invention is desirable to maintain the patency of the pneumostoma and control flow of materials between the exterior of the patient and the parenchymal tissue of the lung via a pneumostoma. The pneumostoma management system includes a pneumostoma management device and a protective cover as described herein.

Pneumostoma Management System Including a Cover

Figure 2A:
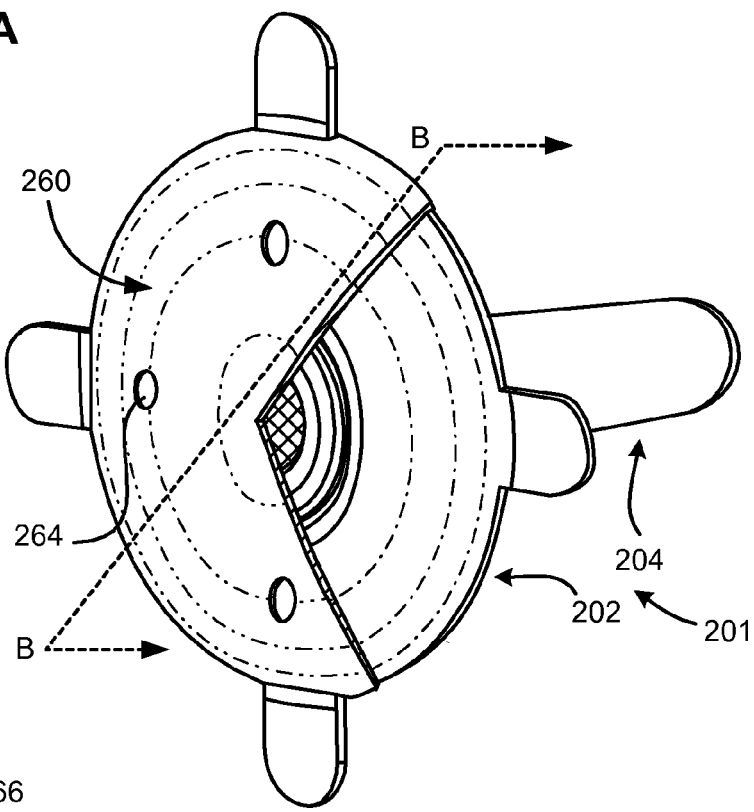
FIG. 2A shows a perspective cutaway view of a pneumostoma management system according to an embodiment of the present invention.
Figure 2B:
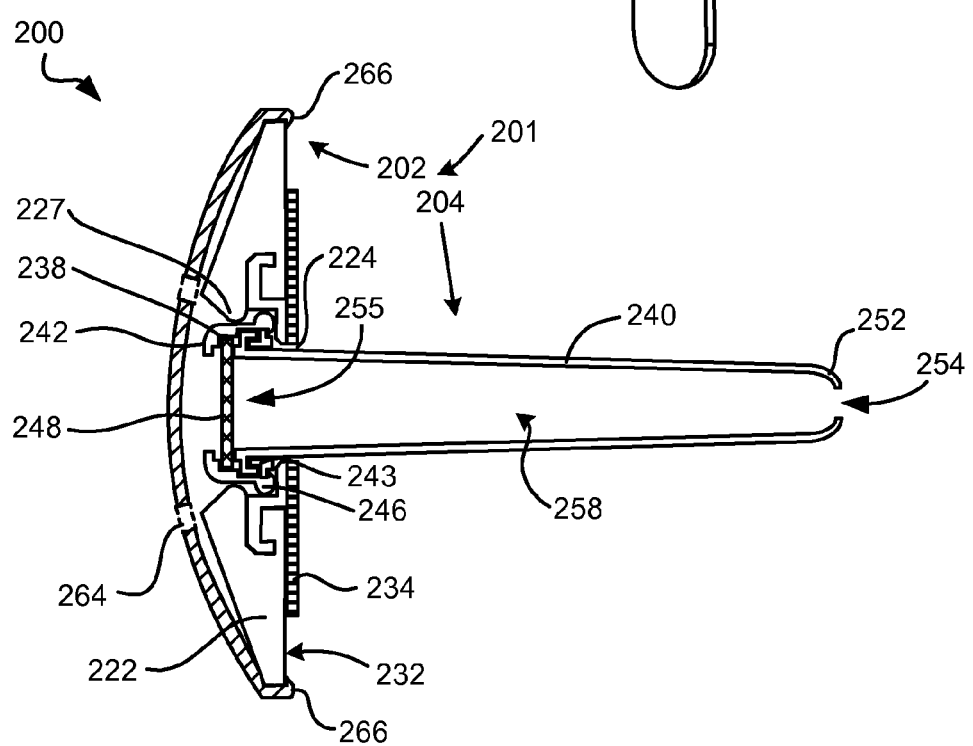
FIG. 2B shows a sectional view of the pneumostoma management system of FIG. 2A.

FIGS. 2A and 2B illustrate views of a pneumostoma management system 200 including a pneumostoma management device ("PMD") 201 and a cover 260 in accordance with an embodiment of the present invention. PMD 201 includes a chest mount 202 which may be mounted to the skin of the patient and a pneumostoma vent 204 which is fitted to the chest mount 202. In a preferred embodiment pneumostoma vent 204 is mounted though an aperture 224 in chest mount 202. Chest mount 202 has a first coupling that engages a second coupling of the pneumostoma vent to releasably secure the pneumostoma vent 204 to the chest mount 202. As will be further described below, the join between the two components of PMD 201 is engineered to ensure that pneumostoma vent 204 cannot be over-inserted into the lung if it separates from chest mount 202.

Referring to FIG. 2A, cover 260 is shown with a partial cutaway to reveal PMD 201. As shown in FIG. 2A, cover 260 fits over chest mount 202 and pneumostoma vent 204. Cover 260 is secured to PMD 201 with clips, adhesive or the like. Cover 260 is generally circular and obscures the majority of the outer surface of PMD 201 when worn by the patient. The outer surface of the cover 260 may serve a protective or cosmetic function.

As shown in FIG. 2A, cover 260 comprises a plurality of apertures 264 through which air may pass to and from pneumostoma vent 204. In some embodiments, cover 260 is designed so that it does not obstruct air flow to and from pneumostoma vent 204. This can be achieved by aligning one or more of apertures 264 with hydrophobic filter 248 (identified in FIG. 2B). However, as shown in FIG. 2B, apertures 264 can be out-of-line with hydrophobic filter 248 and cover 260 can be spaced from cap 242 to allow air flow. The out-of-line apertures 264 of cover 260 serve to protect hydrophobic filter 248 from mechanical injury while still permitting gases to exit the lung.

In preferred embodiments, pneumostoma vent 204 is formed from biocompatible/implantable polymers or biocompatible/implantable metals. In preferred embodiments, chest mount 202 and cover 260 are also formed from biocompatible polymers or biocompatible metals. A patient will typically wear a PMD at all times and thus the materials should meet high standards for biocompatibility. Further description of suitable materials for manufacturing a PMD are provided in the Materials section below.

Referring now to FIG. 2B, the shape of cover 260 corresponds generally to the profile of PMD 201. Cover 260 is preferably retained by PMD 201 by clips, detents, tabs and the like. Cover 260 is preferably press-fit to PMD 201. Cover 260 may also be adhered to PMD 201 using an adhesive, for example, a releasable adhesive. In some embodiments, flange 222 may have features at its perimeter that engage features of cover 260 to retain cover 260. As shown in FIG. 2B, clips 266 of cover 260 engage the perimeter of flange 222 such that cover 260 is securely but releasably held to flange 222. In other embodiments, recess 226 of flange 222 may have features that engage features of cover 260 to retain cover 260.

Pneumostoma vent 204 includes a tube 240 sized and configured to fit within the channel of a pneumostoma. Tube 240 is stiff enough that it may be inserted into a pneumostoma without collapsing. Over time, a pneumostoma may constrict and it is one function of PMD 201 to preserve the patency of the channel of the pneumostoma by resisting the natural tendency of the pneumostoma to constrict. A crush recoverable material may be incorporated into tube 240 in order to make it crush recoverable. In one example, Nitinol, or another superelastic material, incorporated into tube 240 will give the tube collapse resistance and collapse recovery properties.

Tube 240 of pneumostoma vent 204 is sufficiently long that it can pass through the thoracic wall and into the cavity of a pneumostoma inside the lung. Pneumostoma vent 204 is not, however, so long that it penetrates so far into the lung that it might interfere with a major blood vessel. Fortunately, the larger blood vessels of the lung are located centrally and associated with the bronchi. Thus, the pneumostoma will typically only be adjacent to smaller peripheral blood vessels and risk from injury by the pneumostoma vent is small.

The length of tube 240 required for a pneumostoma vent 204 varies significantly between different pneumostomas. A longer tube 240 is usually required in patients with larger amounts of body fat on the chest. A longer tube 240 is usually required where the pneumostoma is placed in the lateral position 112 rather than the frontal position 110 of FIG. 1A. Because of the variation in pneumostomas, pneumostoma vents 204 are manufactured having tubes 240 in a range of sizes and a patient is provided with a pneumostoma vent 204 having a tube 240 of appropriate length for the patient's pneumostoma. Tube 240 may be from 30 to 120 mm in length and from 5 mm to 20 mm in diameter depending on the size of a pneumostoma. A typical tube 240 may be between 40 mm and 80 mm in length and between 8 mm and 12 mm in diameter. In alternative embodiments, a pneumostoma vent 204 is made with a single length (such as 120 mm) of tube 240 and tube 240 is then cut to the length appropriate for a particular patient.

Tube 240 of pneumostoma vent 204 preferably comprises an atraumatic tip 252 at the distal end as shown in FIGS. 2A and 2B. (This application uses the terms proximal and distal regarding the components of the pneumostoma management system in the conventional manner. Thus, proximal refers to the end or side of a device closest to the hand operating the device, whereas distal refers to the end or side of a device furthest from the hand operating the device.) Tip 252 may be rounded, beveled or curved in order to reduce irritation or damage to the tissues of the pneumostoma or lung during insertion or while in position. Where a single length tube 240 is provided and subsequently cut to length it is desirable that the tube be shaped such that at each of a plurality of cut points cutting will generate an atraumatic tip. This can be achieved, for example, by including a series of rounded narrow points on tube 240.

The material and thickness of tube 240 of pneumostoma vent 204 is selected such that tube 240 is soft enough that it will deform rather than cause injury to the pneumostoma or lung. Pneumostoma vent 204 has an opening 254 in tip 252 of tube 240. Opening 254 allows the entry of gases from the cavity of the pneumostoma into lumen 258 of tube 240. Tube 240 is optionally provided with one or more side openings (not shown) positioned near tip 252 and/or along the length of tube 240 to facilitate the flow of gas and/or mucous/discharge into lumen 258.

Pneumostoma vent 204 includes a cap 242 and a hydrophobic filter 248 over the opening 255 in the proximal end of tube 240. Hydrophobic filter 248 is positioned over the proximal opening 255 into lumen 258. Hydrophobic filter 248 is positioned and mounted such that material moving between lumen 258 and the exterior of pneumostoma vent 204 must pass through hydrophobic filter 248. Hydrophobic filter 248 is preferably designed such to fit into a recess in cap 242. As shown in FIG. 2B, cap 242 comprises a recess 238 into which hydrophobic filter 248 may be fit. Hydrophobic filter 248 may, alternatively, be fitted into cap 242 using a joint such as a threaded coupling or adhesive or, in some cases, formed integrally with cap 242. Hydrophobic filter 248 may be made from a material such as medical grade GORE-TEX® (W. L. Gore & Associates, Inc., Flagstaff, Ariz.). As shown in FIG. 2B, a snap ring 243 locks cap 242 and hydrophobic filter 248 onto the proximal end of tube 240.

Hydrophobic filter 248 serves several purposes. In general, hydrophobic filter 248 controls the passage of solid or liquid material between the lumen 258 and the exterior of cap 242. For example, hydrophobic filter 248 prevents the flow of water into the lumen 258 through proximal opening 255. Thus, a patient using PMD 201 may shower without water entering the lung through the pneumostoma. Hydrophobic filter 248 may also be selected so as to prevent the entry of microbes, pollen and other allergens and pathogens into the lumen 258. Hydrophobic filter 248 also prevents the exit of liquid and particulate discharge from lumen 258 to the exterior of pneumostoma vent 204. This is desirable to prevent contact between liquid and particulate discharge and clothing, for example.

Chest mount 202 connects to the proximal end of pneumostoma vent 204. In one embodiment, illustrated in FIGS. 2A and 2B, chest mount 202 comprises a flange 222 and an aperture 224. The aperture 224 is adapted and configured to receive the pneumostoma vent 204. Chest mount 202 is designed to have a smooth surface and a low profile so it is comfortable for the patient to wear. Chest mount 202 should be designed so as not to snag on the patient's clothing or to restrict motion of the patient's arm (if placed in a lateral pneumostoma 112). Flange 222 is significantly wider than pneumostoma vent 204. Flange 222, thus, comprises a contact surface 232 which contacts the skin of the patient surrounding the pneumostoma and positions the aperture 224 over the opening of the pneumostoma. Flange 222 is designed such that it is sufficiently flexible that it can conform to the surface of the chest. Contact surface 232 is also provided with a pad of biocompatible adhesive 234, such as a hydrocolloid adhesive, for securing flange 222 to the skin of the patient. The adhesive 234 may be protected by a protector sheet that is removed prior to use of flange 222. Adhesive 234 should be selected so as to secure flange 222 to the chest of the patient in the correct position relative to the pneumostoma without causing undue irritation to the skin of the patient. The adhesive need not create an air tight seal between flange 222 and the skin of the patient. Suitable adhesive pads are available commercially from Avery Dennison (Painesville, Ohio).

Figure 2C:
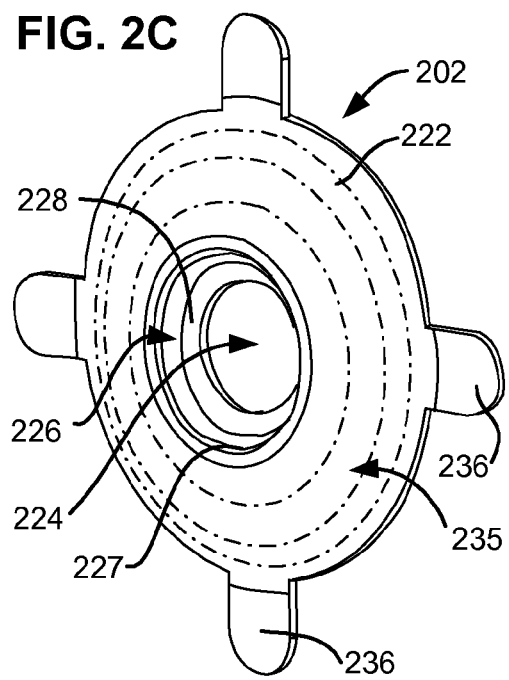
FIG. 2C shows a perspective view of the mounting flange of FIG. 2A.

Referring now to FIG. 2C which shows a perspective view of chest mount 202 without pneumostoma vent 204. Flange 222 is generally circular but is provided with one or more tabs 236 to facilitate application and removal of flange 222 from the skin of the patient. As shown in FIG. 2C, chest mount 202 comprises an aperture 224 through which tube 240 of pneumostoma vent 204 may be inserted. Flange 222 is slightly convex on the upper surface 235. Flange 222 includes a recess 226 into which cap 242 of pneumostoma vent 204 may be press fit. Flange 222 is thick enough in the region of aperture 224 to receive the cap 242 of pneumostoma vent 204 so that the cap of pneumostoma vent 204 is flush with the upper surface 235 of flange 222. Recess 226 forms a coupling adapted to releasably secure the cap 242 of pneumostoma vent 204 into flange 222. As shown in FIGS. 2B and 2C, recess 226 has a lip 227 to releasably secure the cap 242 of pneumostoma vent 204 into flange 222. However, other couplings may be used to releasably secure pneumostoma vent 204 to chest mount 202 including clips, pins, snaps, catches, threaded joints, temporary adhesive and the like. In a preferred embodiment, an aperture plate 228 is embedded in the conformable polymer of flange 222. The aperture plate 228 defines aperture 224 of chest mount 202. Aperture plate 228 is made of a stiffer, less compliant material than flange 222 in order that the dimensions of aperture 224 are tightly controlled. Aperture plate 228 is stiff enough that the size and shape of aperture 224 remains stable even under any likely application of force to chest mount 202.

Figure 2D:
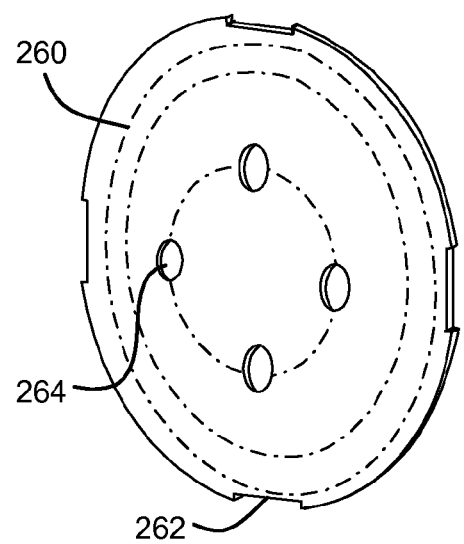
FIG. 2D shows a perspective view of the cover of FIG. 2A.

Referring now to FIG. 2D which shows a perspective view of cover 260. Cover 260 is generally circular but is provided with one or more indents 262 sized and positioned to fit over tabs 236 of flange 222. As shown in FIG. 2D, cover 260 comprises a plurality of apertures 264 through which air may pass to and from pneumostoma vent 204. In some embodiments, cover 260 is designed so that it does not obstruct air flow to and from pneumostoma vent 204. This can be achieved by aligning one or more of apertures 264 with hydrophobic filter 248. However, as shown in FIG. 2A, apertures 264 can be out-of-line with hydrophobic filter 248 and cover 260 can be spaced from cap 242 to allow air flow. Where apertures 264 are out-of-line with hydrophobic filter 248, cover 260 serves to protect hydrophobic filter 248 from mechanical injury.

In alternative embodiments, cover 260 is designed for intermittent use. In such embodiments, cover 260 may partially or completely obstruct the air flow to and from pneumostoma vent 204. Thus, cover 260 may be a protective cover that a patient applies to PMD 201 when the patient engages in activities that might damage hydrophobic filter 248 or expose the patient to noxious gas or vapor which might pass through hydrophobic filter 248 and harm the pneumostoma. Cover 260 may also be a cosmetic cover that a patient applies to PMD 201 when the patient engages in activities or wears clothes which expose the region of the chest where PMD 201 is located (for example, wearing a swimsuit).

Figure 2E:
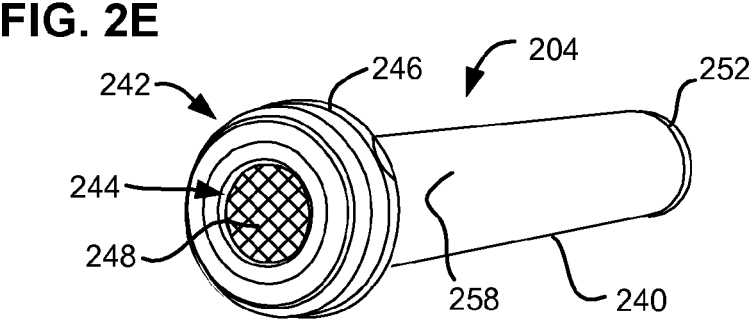
FIG. 2E shows a perspective view of the pneumostoma vent of FIG. 2A.

Referring now to FIG. 2E which shows a perspective view of pneumostoma vent 204 without chest mount 202. Cap 242 is attached to the proximal end of tube 240. Hydrophobic filter 248 is sandwiched between cap 242 and tube 240. An opening 244 in cap 242 communicates with the lumen 258 of tube 240 via hydrophobic filter 248. As shown in FIGS. 2B and 2E, cap 242 comprises a lip 246 which releasably engages lip 227 of recess 226 of flange 222 to secure pneumostoma vent 204 within the recess 226 of flange 222. Lip 246 forms a coupling element of pneumostoma vent 204 that cooperates with recess 226 to releasably secure pneumostoma vent 204 into chest mount 202 with tube 240 positioned through aperture 224.

Figure 2F:
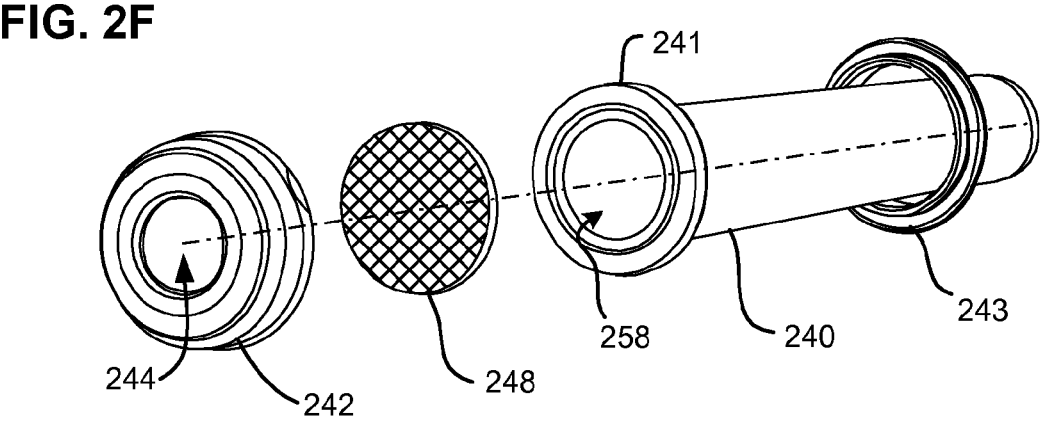
FIG. 2F shows an exploded perspective view of the pneumostoma vent of FIG. 2E.

FIG. 2F shows an exploded view of pneumostoma vent 204 showing the individual components of pneumostoma vent 204. Hydrophobic filter 248 is sandwiched between tube 240 and cap 242. Tube 240 has a flange 241 at its proximal end. Snap ring 243 slides over tube 240. The inner diameter of snap ring 243 is too small to pass over flange 241, thus, when snap ring 243 is locked into cap 242, tube 240 is locked to cap 242. It should be noted that the outer diameter of each of snap ring 243, hydrophobic filter 248, flange 241 and cap 242 is larger than the diameter of aperture 224 of aperture plate 228. Aperture plate 228 is sufficiently stiff that the dimensions of aperture 224 will not change even under loads significantly higher than would be expected during use of the device. Thus, snap ring 243, hydrophobic filter 248, flange 241 and cap 242 cannot pass through aperture 224 into the pneumostoma. Distal tip 252 of tube 240 and the body of tube 240 are small enough to pass through aperture 224 however, flange 241 and/or cap 242 serve to limit the passage of tube 240 through aperture 224. These safety features prevent unsafe entry of any of the components of pneumostoma vent 204 into the pneumostoma even in the unlikely event of device failure. Likewise, all the components of the chest mount 202 including flange 222 and aperture plate 228 are significantly larger than the aperture of a pneumostoma, thus, precluding passage of any component of the chest mount 202 into a pneumostoma even in the unlikely event of device failure.

Use of a Pneumostoma Management System Having a Cover

Figure 3A:
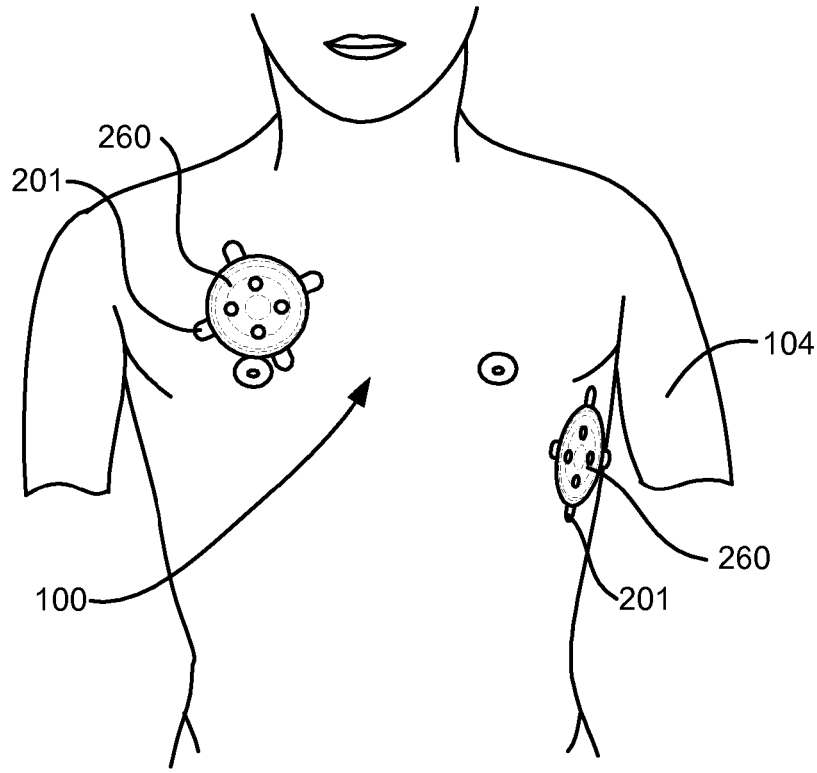
FIG. 3A shows the chest of a patient showing the positioning of the pneumostoma management system of the present invention.

FIG. 3A illustrates the positioning of pneumostoma management system 200 over pneumostoma 110 and pneumostoma 112 of FIG. 1A. As shown in FIG. 3A, the low profile of the pneumostoma management system 200 allows it to be inconspicuously positioned on the chest 100 of a patient in either the frontal 110 or lateral 112 locations. The pneumostoma management system 200 is designed so as not to interfere with the range of motion or clothing of the patient. The cover 260 of pneumostoma management system 200 is designed to provide a protective and/or cosmetic exterior to PMD 201. This is of importance for a device such as PMD 201 which must be used continuously to be effective. Comfort, ease of use and patient acceptance are important if patient compliance with treatment protocols is to be achieved.

To use PMD 201, chest mount 202 is first positioned over a pneumostoma and secured with adhesive to the skin of the patient. In a preferred embodiment, the chest mount remains attached for up to a week thereby avoiding irritation of the skin caused by daily attachment and removal of a mount. Chest mount 202 may be positioned by the patient by manual alignment of the aperture 224 of chest mount 202 with the aperture of the pneumostoma. Alternatively, a pneumostoma vent or an alignment tool may be used to align the chest mount. Cover 260 may be secured to PMD 201 after PMD 201 has been correctly positioned relative to the pneumostoma.

As shown in FIG. 3A, cover 260 covers all or almost all of PMD 201. Thus, cover 260 can serve a number of purposes. First, cover 260 can protect PMD 201, and, in particular, pneumostoma vent 204 (not shown in this view) from damage. Second, cover 260 can conceal PMD 201 by presenting an exterior surface that is colored to match the patient's skin tone. A number of covers 260 may be provided in a range of colors from which a patient may select a color that most closely matches their skin-tone at the implant location. Alternatively, cover 260 may be custom colored to more closely match the patient's skin-tone. Alternatively, the color of cover 260 may be selected so as to be inconspicuous relative to the clothing of the patient. Thus, the color of cover 260 may be selected to be a matching color or complimentary color to the patient's clothing. Cover 260 may be colored blue, for example, to match blue clothing. The patient may be supplied with a variety of covers to choose from depending on their clothing for a day.

In alternative embodiments, cover 260 may be embellished rather than concealed so as to appear to comprise jewelry, a tattoo or the like. Additionally, cover 260 may be made available in a wide variety of colors and styles without changing the underlying PMD 201. This is important as alteration to PMD 201 may require regulatory approval. The different options for the appearance of cover 260, allow the patient to be comfortable with the PMD without being self conscious. Patient comfort and confidence promotes compliance with protocols for the maintenance of the pneumostoma thereby promoting the health of the patient.

Figure 3B:
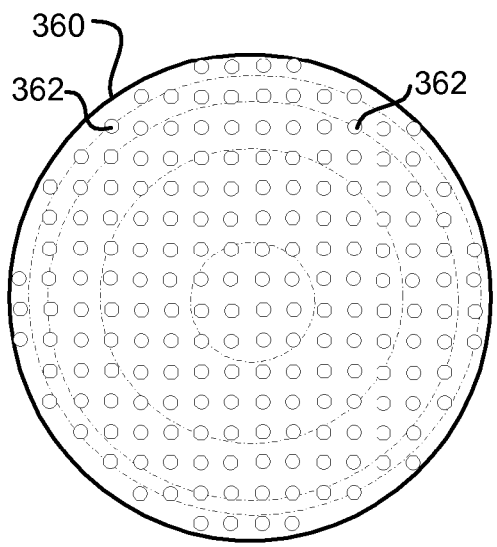
FIG. 3B shows an alternative cover according to an embodiment of the present invention.
Figure 3C:
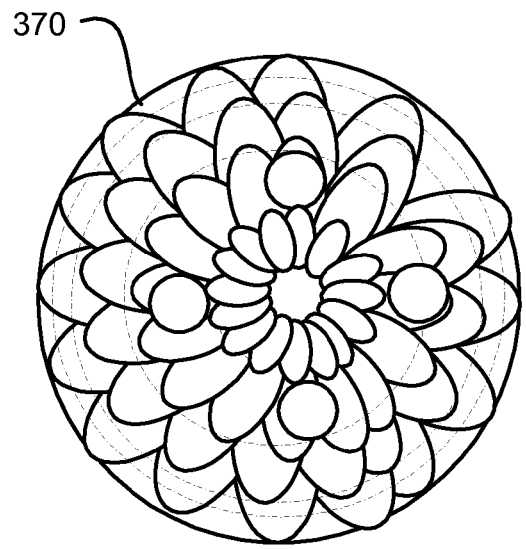
FIG. 3C shows an alternative cover according to an embodiment of the present invention.

FIG. 3B shows an alternative cover 360 in which the cover comprises a large number of small apertures 362. Apertures 362 may be approximately 2 mm or less in diameter. Where apertures 362 are sufficiently small they will not be noticeable to the casual observer and will not interfere with the function or cosmetic appearance of cover 360. However, where there are a large number of small apertures 362, the apertures, as a group, will allow for sufficient air flow in and out of the pneumostoma vent without undue resistance. FIG. 3C illustrates an alternative cover 370 having an ornamental design in the form of a flower. Cover 370 provides an example of an embellished cover rather than a concealing cover. The ornamental design may be selected from a range of ornamental designs or may be customized by the patient or to the patient's requirements. In some cases, the ornamental design may be printed on a preformed cover using a printer adapted (if necessary) to print on the shape of the surface of the cover.

In some cases, the pneumostoma management device is replaced periodically such as weekly and/or daily. Covers may be designed so that they may be removed from the pneumostoma management device and then reused on the next pneumostoma management device. Thus, the cover, may, in some circumstances, be used for a period of time significantly longer than the components of the PMD which are in direct contact with the patient. Preferably, the cover will be made of a material that may be cleaned from time to time. Alternative covers may be designed to be disposable.

Alternative Pneumostoma Management Systems Having Covers

Cover 260 may be adapted for pneumostoma management devices of different designs including, for example, those pneumostoma management devices discussed in the related applications incorporated by reference above. The cover obscures and/or protects the majority of the exposed surface of the pneumostoma management device without interfering with the function of the device. The cover is permanently or releasably attachable to the pneumostoma management device, using adhesives or fasteners. The cover can then provide a protective or cosmetic function as previously described.

Figure 4A:
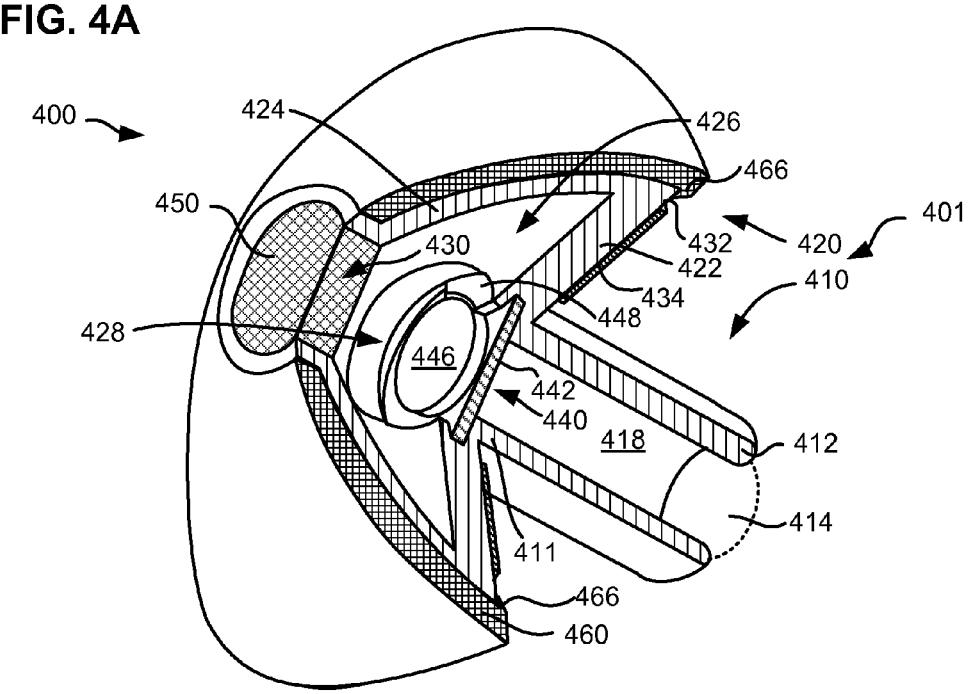
FIG. 4A shows a perspective cutaway view of an alternative pneumostoma management system having a cover according to an embodiment of the present invention.

FIG. 4A illustrates an alternative pneumostoma management system 400 including a cover 460 and a pneumostoma management device ("PMD") 401 in accordance with an embodiment of the present invention. PMD 401 comprises an implantable sleeve 410 joined at its proximal end 411 with a bulb 420 which may be mounted to the skin of the patient. In a preferred embodiment, sleeve 410 is formed in one piece with bulb 420. In preferred embodiments, cover 460, sleeve 410 and bulb 420 are formed from biocompatible polymers or a biocompatible metal such stainless steel.

Sleeve 410 preferably comprises a rounded distal tip 412 in order to reduce irritation or damage to the tissues of the pneumostoma or lung during insertion or while in position as shown in FIG. 4A. Sleeve 410 has an opening 414 in tip 412. Opening 414 allows the entry of gases from the cavity of the pneumostoma into sleeve 410, and, thence, via the lumen 418 of sleeve 410 to the bulb 420.

Figure 4B:
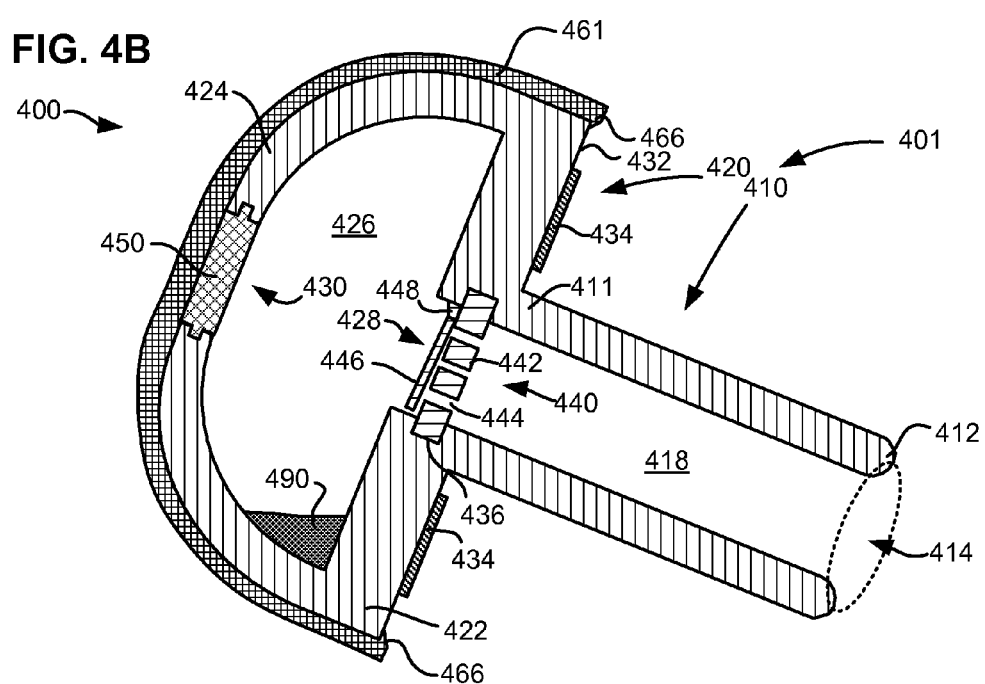
FIG. 4B shows a sectional view of the pneumostoma management system of FIG. 4A having an alternative cover.

Bulb 420 is connected to the proximal end 411 of sleeve 410. In one embodiment, illustrated in FIGS. 4A and 4B, bulb 420 comprises a flange 422 and a dome 424. The flange 422 and dome 424 define a chamber 426. The chamber 426 has an entrance aperture 428 and at least one exit aperture 430. Exhaled air and solid material may flow from lumen 418 of sleeve 410 into chamber 426 through entrance aperture 428. Exhaled air may exit chamber 426 through exit aperture 430 to vent to atmosphere outside of the patient's body. For simplicity of manufacturing, flange 422 and dome 424 may be formed in one piece as shown in FIG. 4B. Bulb 420 has a smooth surface and a low profile so it is comfortable for the patient to wear. Bulb 420 is designed so as not to snag on the patient's clothing or to restrict motion of the patient. Chamber 426 is sized and configured to receive liquid and/or solid material 490 such as mucous which may be exhaled from the lung through the pneumostoma 110.

Flange 422 is significantly wider than sleeve 410. Flange 422, thus, comprises a contact surface 432 perpendicular to sleeve 410 and surrounding sleeve 410 which, when the sleeve 410 of PMD 401 is positioned in a pneumostoma 110, will contact the skin of the patient surrounding pneumostoma 110. The contact surface 432 serves as an insertion limit to prevent over-insertion of sleeve 410 into a pneumostoma 110. Contact surface 432 is provided with a biocompatible adhesive 434, such as a hydrocolloid adhesive, for securing PMD 401 to the skin 114 of the patient. Adhesive 434 should be selected so as to help maintain the correct position of PMD 401 without causing undue irritation to the skin of the patient.

A flow control device 440 is positioned in aperture 428 between lumen 418 of sleeve 410 and chamber 426. Flow control device 440 is positioned and mounted such that material moving between lumen 418 and chamber 426 must pass through flow control device 440. In the embodiment shown in FIGS. 4A and 4B, flange 422 is provided with a recess 436 into which flow control device 440 may be mounted.

Flow control device 440 may comprise a one-way valve assembly such as a flapper valve, Heimlich valve, reed valve, or the like, for allowing air to be exhaled through entrance aperture 428 into chamber 426 while restricting the flow of air or other matter into lumen 418 from chamber 426. It is desirable to restrict flow of air in through the pneumostoma so as to encourage a reduction in hyperinflation and to prevent the inhalation of solid or liquid matter from into the lung through the pneumostoma. The flow control device 440, shown in FIG. 4B, comprises a fixed disc 442 having a number of apertures 444. Above fixed disc 442 is a flapper disc 446. Flapper disc 446 is kept in place above fixed disc 442 by hinge 448. When the air pressure in lumen 418 is greater than the air pressure in chamber 426 during exhalation, flapper disc 446 moves away from fixed disc 442 and air may pass through a space between fixed disc 442 and flapper disc 446 and enter chamber 426 from lumen 418. However, when the air pressure in lumen 418 is less than the air pressure in chamber 426 during inhalation, flapper disc 446 moves towards fixed disc 442 and obstructs the apertures 444 in fixed disc 442 such that no air may pass into lumen 418 from chamber 426.

A hydrophobic filter 450 is positioned in exit aperture 430 between chamber 426 and the exterior of bulb 420. Hydrophobic filter 450 is positioned and mounted such that material moving between chamber 426 and the exterior of bulb 420 must pass through hydrophobic filter 450. Hydrophobic filter 450 prevents the flow of water in and out of chamber 426 through exit aperture 430. In the embodiment shown in FIGS. 4A and 4B, flange 422 is provided with a recess 436 into which flow control device 440 may be press fit.

Cover 460 comprises a plurality of clips 466 to releasably hold cover 460 onto the surface of dome 424. PMD 401 may be a disposable device and cover 460 may either be a disposable cover or may be reusable. Where cover 460 is disposable, it may be preferable to attach cover 460 to dome 424 using a permanent adhesive, non-releasable clips or the like. Cover 460 has an aperture 462 that is aligned with and sized to fit around a lip surrounding hydrophobic filter 450. Thus, cover 460 does not interfere with the flow of air through hydrophobic filter 450. Note that when in use, no part of cover 460 is in contact with the patient or directly exposed to the interior of chamber 426. Cover 460 may be designed to serve any of the purposes previously discussed with respect to e.g. covers 260, 360 and 370.

As shown in FIG. 4B, a cover 461 may also be designed to have no apertures, and, thus, block hydrophobic filter 450 temporarily. Cover 461 is held in contact with dome 424 by releasable clips 466. Cover 461 prevents flow of air through hydrophobic filter 450, and, thus, must be removed to allow air to flow through the pneumostoma. The cover 461, shown in FIG. 4B, is useful to temporarily protect hydrophobic filter 450 from contamination or damage or to temporarily prevent flow of gases in and out of a pneumostoma. Cover 461 may be used, for example, while a patient is swimming to protect filter 450 and safeguard against entry of water or other contaminants into chamber 426. Note that when in use, no part of cover 461 is in contact with the patient or directly exposed to the interior of chamber 426. An alternative cover 461 may be made of a porous material through which air may exit bulb 420 despite the absence of apertures.

Figure 5A:
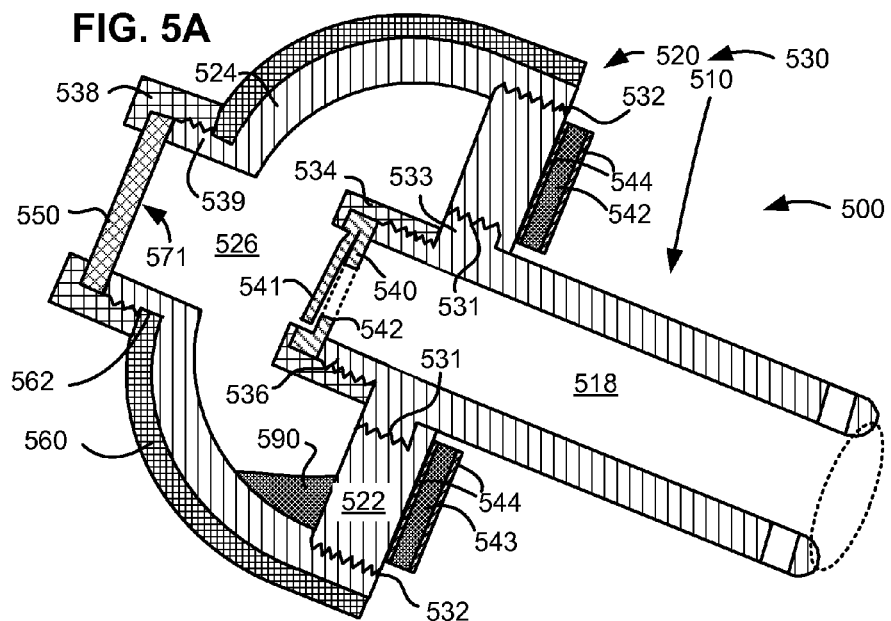
FIGS. 5A-5B show views of an alternative pneumostoma management system having a cover according to an embodiment of the present invention.
Figure 5B:
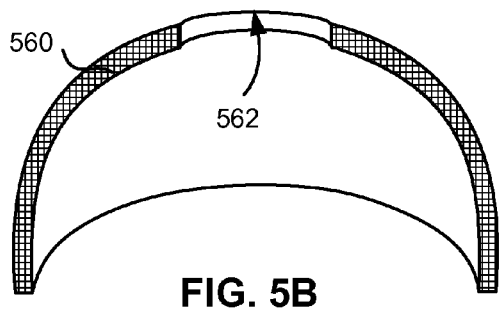

FIG. 5A illustrates an alternative pneumostoma management system 500 comprising a PMD 530 and cover 560. FIG. 5B shows a perspective cutaway view of cover 560 of FIG. 5A. As shown in FIG. 5A, PMD 530 has several threaded fittings to permit PMD 530 to be dismantled for cleaning and sterilization. Removable dome 524 is attached to flange 522 of bulb 520 by threaded joint 532. Threaded joint 532 allows dome 524 to be removed from flange 522 to allow entry to chamber 526 for cleaning/sterilization purposes and for access to flow-control device 540. Chamber 526 is sized and configured to receive liquid and/or solid material 590 such as mucous which may be exhaled from the lung through the pneumostoma 110. As shown in FIG. 5A, sleeve 510 is attached to flange 522 by threaded joint 531. Note that sleeve 510 must be installed through flange 522 and shoulder 533 prevents separation of sleeve 510 into the pneumostoma. Because sleeve 510 may be separated from flange 522, a number of sleeves 510 of different lengths and/or diameters as required for pneumostomas of different size may be manufactured and mated with a standard bulb 520. Likewise, a second threaded cap 538 secures hydrophobic filter 550 over the exit aperture 571 from chamber 526. Threaded cap 538 mounts to threaded fitting 539 of removable dome 524 trapping hydrophobic filter 550 between threaded cap 538 and threaded fitting 539. Threaded cap 538 may, thus, be removed to allow cleaning and/or replacement of hydrophobic filter 550. Hydrophobic filter 550 may be a disposable component that is replaced upon each use of sterilizable PMD 530 or it may also be reusable.

Referring again to FIG. 5A, flow-control device 540 is held in position over lumen 518 by a threaded cap 534. Threaded cap 534 mounts to threaded fitting 536 trapping flow-control device 540 between threaded cap 534 and threaded fitting 536. When dome 524 is removed, threaded cap 534 may also be removed allowing flow-control device 540 to be cleaned and/or replaced. Flow-control device 540 is shown in FIG. 5A as a simple flapper valve having a hinged flap 541 over a plate 542 with an aperture. As shown in FIG. 5A, the flap 541 may be connected to the aperture plate 542 by a living hinge. Flow-control device 540 may be a disposable component that is replaced upon each use of sterilizable PMD 530 or it may also be reusable. Flow control device 540 allows gasses to exit lumen 518 into dome 524 but blocks the materials from entering lumen 518 from dome 524.

Referring again to FIG. 5A, cover 560 covers the outer surface of dome 524. Cover 560 has an aperture 562 (shown in detail in FIG. 5B) to fit over threaded fitting 539 of dome 524. Aperture 562 is sufficiently small that when threaded cap 538 is screwed onto threaded fitting 539, cover 560 is trapped between threaded cap 538 and dome 524. Thus, cover 560 requires no clips or adhesive to secure cover 560 in position over dome 524. Also, no part of cover 560 is in contact with the patient or directly exposed to the interior of chamber 526. Cover 560 may be designed for the purposes previously discussed including, for example, concealment, ornamentation or protection of PMD 530.

PMD 530 of FIG. 5A is intended for sterilization and reuse; it is preferable that the reusable components such as sleeve 510, flange 522 and dome 524 be made of a biocompatible metal material such as stainless steel (or a sterilizable polymer). Cover 560 may be made of a biocompatible polymer but there may be more flexibility in material selection for cover 560 because cover 560 does not contact the patient directly. Thus, where dome 524 is made of, e.g. steel, cover 560 may be made from a polymer which is available in a range of colors and/or textures.

Hydrophobic filter 550 is preferably a disposable component. Because flange 522 may not be conformable if made of e.g. steel, an annular conformable pad 543 is provided to fit between flange 522 and the skin of the patient. The conformable pad 543 is preferable disposable and may comprise a layer of biocompatible adhesive 544 on each side to hold it to flange 522 and the skin of the patient. Each annular conformable pad 543 preferably comprises a laminate structure with an inner conformable plastic, paper or foam layer (e.g., closed-cell polyethylene foam) sandwiched between adhesive layers 544. Such foam with an adhesive layer is available commercially from Avery Dennison (Painsville, Ohio). Threaded caps 534 and 538 and flow-control device 540 may also be made of reusable components.

Figure 5C:
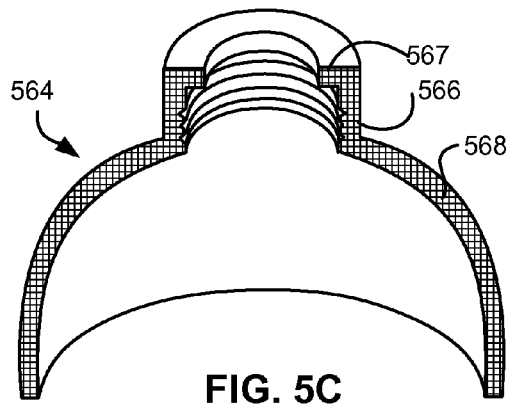
FIG. 5C shows an alternative cover for the pneumostoma management system of FIG. 5A.

FIG. 5C shows a perspective cutaway view of an alternative embodiment of threaded cap 538 in which the threaded cap is integrated with a cover. The threaded cover 564 of FIG. 5C can be used in place of the threaded cap 538 and cover 560 of FIG. 5A. As shown in FIG. 5C, threaded cover 564 comprises a threaded fitting 566 connected to a dome 568. Threaded fitting 566 is designed to mate with a threaded fitting of the PMD such as threaded fitting 539 of FIG. 5A. Threaded fitting 566 has a lip 567 for retaining hydrophobic filter 550 against threaded fitting 539. Threaded fitting 566 may be formed in one piece with dome 568 or formed separately and then joined to dome 568. Note that when in use, no part of threaded cover 564 is in contact with the patient or directly exposed to the interior of chamber 526.

Figure 6A:
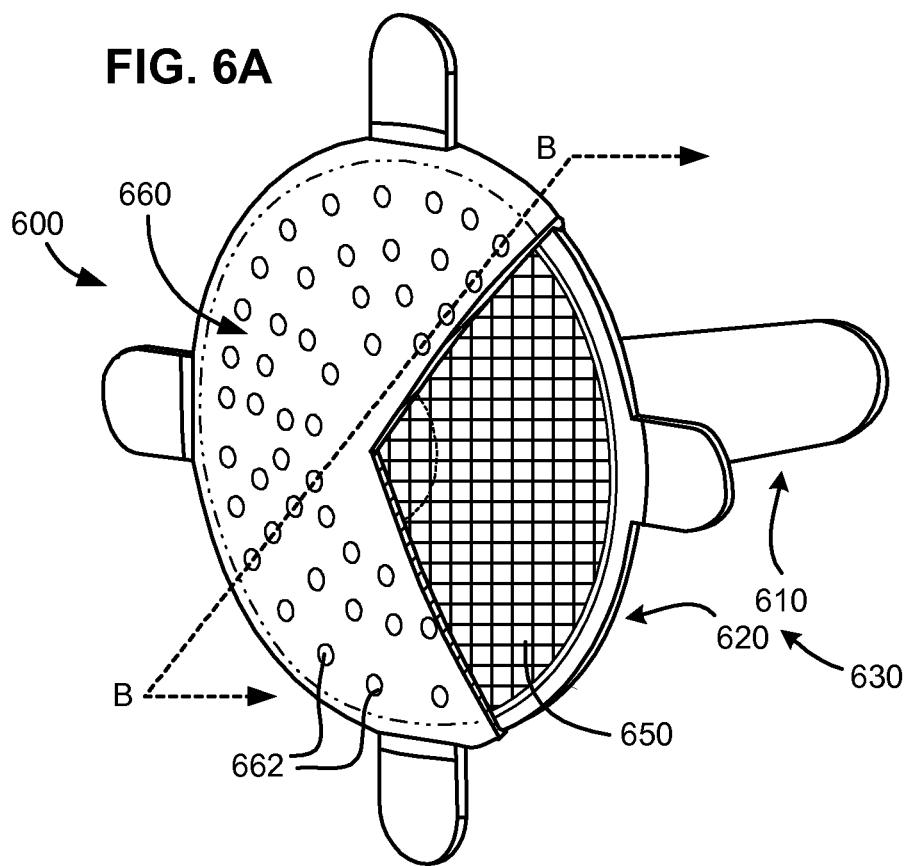
FIGS. 6A-6B show views of an alternative pneumostoma management system having a cover according to an embodiment of the present invention.
Figure 6B:
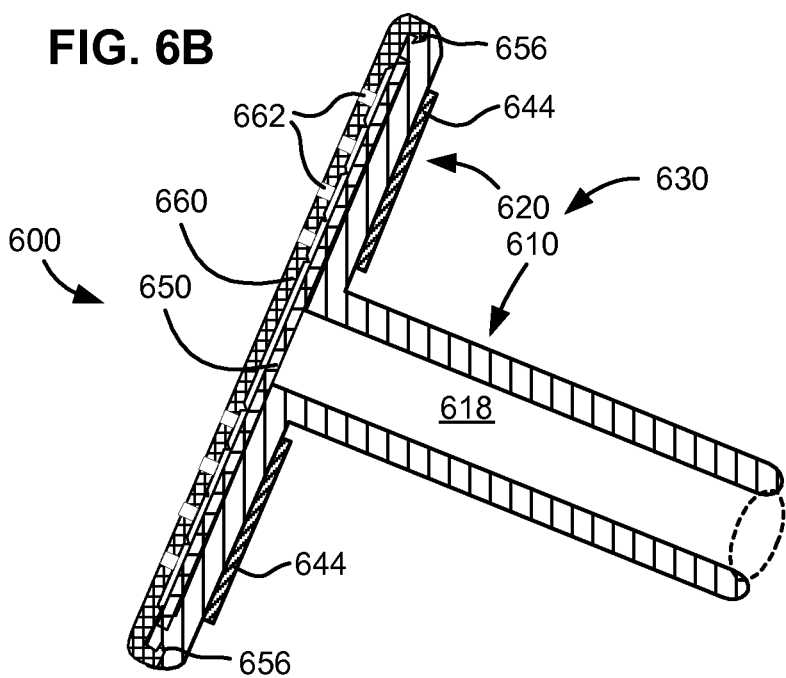

FIG. 6A illustrates an alternative pneumostoma management system 600 comprising a PMD 630 and cover 660. FIG. 6B shows a sectional view through PMD 630 and cover 660 along the line B-B of FIG. 6A. As shown in FIGS. 6A and 6B, PMD 630 has only two components. Flange 620 and sleeve 610 are formed in one piece and comprise the first component. The second component is hydrophobic filter disc 650 which may be free-floating or attached to flange 620 (for example, by press fitting or adhesive). Flange 620 is thin and flexible in order to conform to the skin of the chest of the subject. A biocompatible adhesive 644 is provided to attach flange 620 to the skin of the patient.

Referring again to FIGS. 6A and 6B, cover 660 is preferably press fit to flange 620 and held in place by a plurality of clips 656 at the perimeter. Alternatively cover 660 may be attached to flange 620 by adhesive and/or welding for example. Hydrophobic filter disc 650 is sandwiched between cover 660 and flange 620. Cover 660 and/or flange 620 may be recessed to accommodate hydrophobic filter disc 650. Cover 660 is preferably thin and flexible so that the device may conform readily to the skin of the patient with the cover in place. Thus, in the preferred embodiment cover 660 requires no clips or adhesive to secure cover 660 in position over flange 620. Also, no part of cover 660 is in contact with the patient or directly exposed to the interior of sleeve 610. Cover 660 may be designed for the purposes previously discussed including, for example, concealment, ornamentation or protection of PMD 630.

Referring again to FIGS. 6A and 6B, cover 660 has a plurality of holes 662. However, there are no holes in the center region of cover 660 over the opening to lumen 618 of sleeve 610. During exhalation gasses pass radially from the opening in lumen 618 through holes 662. However, during inhalation, cover 660 is designed to deflect towards flange 620 thereby obstructing lumen 618 and preventing air from flowing into the pneumostoma. Alternatively, or additionally, the center region of hydrophobic filter disc 650 may be treated so that it does not transmit air. The deflection of hydrophobic filter disc 650 would then serve to allow exit of gases from lumen 618 during inhalation and prevent entry of gases during inhalation. Thus, cover 660 and/or filter 650 serve as a one-way valve structure in addition to their other functions. In alternative embodiments, PMD 630 may be designed without the one-way valve features in which case some air may enter the lung through PMD 630 during inhalation.

Figure 7A:
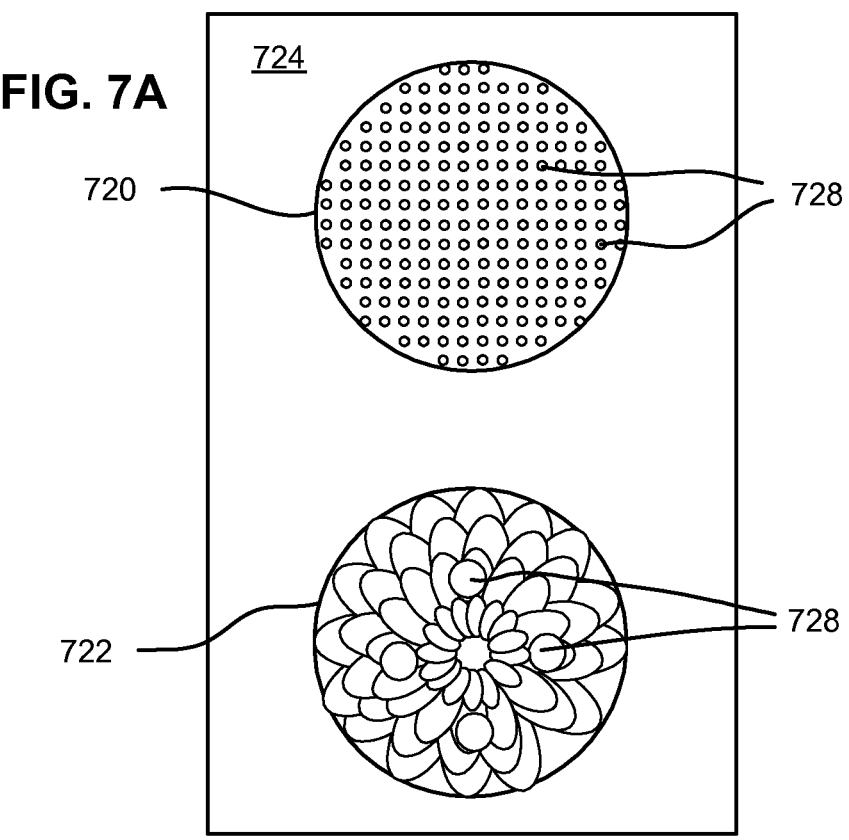
FIGS. 7A-7B show views of an alternative pneumostoma management system having a cover according to an embodiment of the present invention.

In some embodiments, the cover may be made of thin flexible adhesive materials which may be printed and/or colored and then applied to the pneumostoma management device in the same way as a decal. FIG. 7A shows the printing of covers 720, 722 on a precut sheet 724. Sheet 724 is precut around covers 720, 722 such that they may be peeled away from sheet 724 after they have been printed. Apertures 728 are precut in covers 720, 722 and remain adhered to sheet 724 when the covers are peeled away. In some embodiments sheet 724 may be made of a compliant polymer with an adhesive backing such that it may be adhered to the surface of a pneumostoma management device after customization. Printing covers in response to patient requests and/or needs allows a wide range of different colors and/or patterns of covers to be made available to the patient.

Figure 7B:
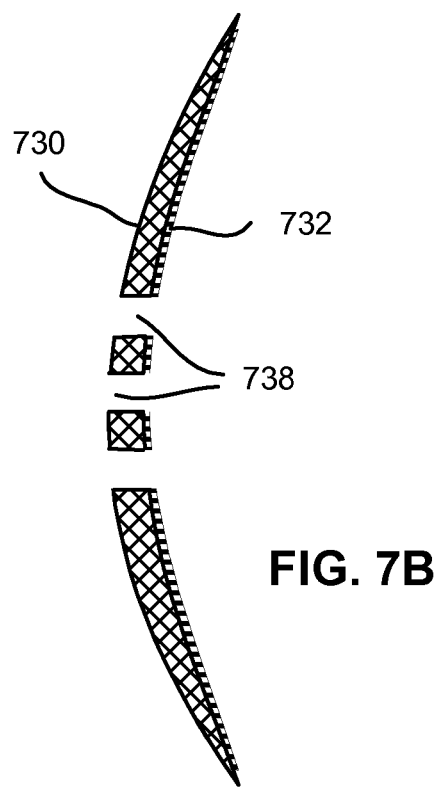

FIG. 7B shows a sectional view of a cover 730 made from a thin flexible material. Cover 730, although compliant, is contoured such that is fits a pneumostoma management device having a curved upper surface without distortion/wrinkling. Cover 730 has an adhesive 732 on the rear surface to bond the cover to the pneumostoma management device. The adhesive surface may be masked with a protective film prior to use. Cover 730 also has a plurality of precut apertures 738 to allow air to exit the pneumostoma management device. Cover 730 may be made, for example, of a foam and/or compliant material or a composite of a thin polymer plus a foam and/or compliant material.

Materials

In preferred embodiments, the pneumostoma vent, chest mount and cover of a pneumostoma management system are formed from biocompatible polymers or biocompatible metals. A patient will typically wear a PMD at all times, and, thus, the materials, particularly of tube 240, should meet high standards for biocompatibility. In general, preferred materials for manufacturing a PMD are biocompatible thermoplastic elastomers that are readily utilized in injection molding and extrusion processing. As will be appreciated, other suitable similarly biocompatible thermoplastic or thermoplastic polymer materials can be used without departing from the scope of the invention. Biocompatible polymers for manufacturing PMD may be selected from the group consisting of polyethylenes (HDPE), polyvinyl chloride, polyacrylates (polyethyl acrylate and polymethyl acrylate, polymethyl methacrylate, polymethyl-coethyl acrylate, ethylene/ethyl acrylate), polycarbonate urethane (BIONATE®), polysiloxanes (silicones), polytetrafluoroethylene (PTFE, GORE-TEX®, ethylene/chlorotrifluoroethylene copolymer, aliphatic polyesters, ethylene/tetrafluoroethylene copolymer), polyketones (polyaryletheretherketone, polyetheretherketone, polyetherether-ketoneketone, polyetherketoneetherketoneketone polyetherketone), polyether block amides (PEBAX®, PEBA), polyamides (polyamideimide, PA-11, PA-12, PA-46, PA-66), polyetherimide, polyether sulfone, poly(iso)butylene, polyvinyl chloride, polyvinyl fluoride, polyvinyl alcohol, polyurethane, polybutylene terephthalate, polyphosphazenes, nylon, polypropylene, polybutester, nylon and polyester, polymer foams (from carbonates, styrene, for example) as well as the copolymers and blends of the classes listed and/or the class of thermoplastics and elastomers in general. Reference to appropriate polymers that can be used for manufacturing PMD 201 can be found in the following documents: PCT Publication WO 02/02158, entitled "Bio-Compatible Polymeric Materials;" PCT Publication WO 02/00275, entitled "Bio-Compatible Polymeric Materials;" and, PCT Publication WO 02/00270, entitled "Bio-Compatible Polymeric Materials" all of which are incorporated herein by reference. Other suitable materials for the manufacture of the PMD include medical grade inorganic materials such stainless steel, titanium, ceramics and coated materials.

Hydrophobic filter materials should be sufficiently porous to allow air to exit through the filter. Materials for hydrophobic filters are available commercially and filters can be fabricated from any suitable hydrophobic polymer, such as tetrafluoroethylene, PTFE, polyolefins, microglass, polyethylene and polypropylene or a mixture thereof. In preferred examples, the hydrophobic filter is a laminated tetrafluoroethylene e.g. TEFLON®, (E.I. du Pont de Nemours Co.) or GORE-TEX® (W.L. Gore, Inc.) of a controlled pore size. In other examples, the hydrophobic filter may comprise a felted polypropylene; PTFE/polypropylene filter media. The hydrophobic filter material may additionally comprise an antimicrobial, an anti-bacterial, and/or an anti-viral material or agent.

In general, the various covers disclosed in this application are designed such that they do not contact the pneumostoma. Thus, the materials of the cover do not have to meet the same high standards for biocompatible and implantable materials as the remainder of the pneumostoma management device. However, the preferred materials for making the covers include medical grade metals, plastics, acrylics and resins. In a preferred embodiment, the cover is made from medical grade ABS (Acrylonitrile-Butadiene-Styrene) plastic colored or painted as required for the application. In some embodiments, the cover may be made of thin flexible adhesive materials which may be printed and/or colored and then applied to the pneumostoma management device in the same way as a decal.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. Embodiments of the present invention may use some or all of the features shown in the various disclosed embodiments where such features are not structurally or functionally incompatible. It is intended that the scope of the invention be defined by the claims and their equivalents.

What is claimed is:

1. A pneumostoma management system comprising:
a cover and a pneumostoma management device;
wherein the pneumostoma management device comprises a tube adapted to be inserted in a pneumostoma, said tube connected to an external section in order to secure the pneumostoma management device to a chest of a patient;
wherein the cover includes a plurality of patient selectable covers, wherein each of the said patient selectable covers is different in appearance;
wherein the cover is configured to detachably attach to and conform to the pneumostoma management device such that said cover presents an outward surface which substantially obscures the external section of the pneumostoma management device from view of a non-patient;
wherein the outward surface of the cover is designed to have a preferred visual appearance for the patient compared to the external section of the pneumostoma management device.

2. The pneumostoma management system of claim 1, wherein the cover comprises one or more clips configured to releasably attach the cover to and conform to the pneumostoma management device.

3. The pneumostoma management system of claim 1, wherein the cover comprises an adhesive surface configured to detachably attach the cover to and conform to the pneumostoma management device.

4. The pneumostoma management system of claim 1, further comprising a threaded coupling that can releasably attach the cover to and conform to the pneumostoma management device.

5. The pneumostoma management system of claim 1, wherein the cover comprises one or more apertures to allow gases to escape from the pneumostoma management device.

6. The pneumostoma management system of claim 1, wherein the outward surface of the cover is color-matched with a skin color of a patient in order for the cover to have a preferred visual appearance for the patient compared to the external section of the pneumostoma management device.

7. The pneumostoma management system of claim 1, wherein the outward surface of the cover is provided with an ornamental pattern in order for the cover to have a preferred visual appearance for the patient compared to the external section of the pneumostoma management device.

8. The pneumostoma management system of claim 1, wherein the outward surface of the cover is provided with a patient-customizable pattern in order for the cover to have a preferred visual appearance for the patient compared to the external section of the pneumostoma management device.

9. The pneumostoma management system of claim 1, wherein the outward surface of the cover is a printable surface and wherein at least one of a customizable pattern and color is printed on the outward surface prior to use of the cover in order for the cover to have a preferred visual appearance for the patient compared to the external section of the pneumostoma management device.

10. The pneumostoma management system of claim 1, wherein the cover comprises a plurality of apertures which are large enough to allow gases to escape from the pneumostoma management device but are each 1 mm or less in diameter.

11. The system of claim 1 wherein said tube includes an aperture that is adapted to communicate with the lung of a patient; and
    said cover can be placed over said aperture in order to close said aperture.

12. A cover for a pneumostoma management device wherein the pneumostoma management device comprises a tube adapted to be inserted in a pneumostoma, said tube connected to an external section in order to secure the pneumostoma management device to a chest of a patient and wherein the cover comprises:
    a body having an outward surface and an attachment surface;
    wherein the cover includes a plurality of patient selectable covers, wherein each of the said patient selectable covers is different in appearance;
    wherein the attachment surface is configured to detachably attach the cover to and conform to a pneumostoma management device;
    wherein the outward surface is adapted to substantially obscure the external section of the pneumostoma management device from view of a non-patient;
    wherein the outward surface of the body is designed to have a preferred visual appearance for the patient compared to the external section of the pneumostoma management device.

13. The cover of claim 12, wherein the attachment surface of the cover comprises one or more clips configured to releasably attach the cover to and conform to the pneumostoma management device.

14. The cover of claim 12, wherein the attachment surface of the cover comprises an adhesive surface configured to detachably attach the cover to and conform to the pneumostoma management device.

15. The cover of claim 12, wherein the cover comprises one or more apertures to allow gases to escape from the pneumostoma management device.

16. The cover of claim 12, wherein the outward surface of the cover is color-matched with a skin color of a patient in order for the cover to have a preferred visual appearance for the patient compared to the external section of the pneumostoma management device.

17. The cover of claim 12, wherein the outward surface of the cover is provided with an ornamental pattern in order for the cover to have a preferred visual appearance for the patient compared to the external section of the pneumostoma management device.

18. The cover of claim 12, wherein the outward surface of the cover is provided with a patient-customizable pattern in order for the cover to have a preferred visual appearance for the patient compared to the external section of the pneumostoma management device.

19. The cover of claim 12, wherein the outward surface of the cover is a printable surface and wherein at least one of a customizable pattern and color is printed on the outward surface prior to use of the cover in order for the cover to have a preferred visual appearance for the patient compared to the external section of the pneumostoma management device.

20. The cover of claim 12, wherein the cover comprises a plurality of apertures which are large enough in aggregation to allow gases to escape from the pneumostoma management device but are each 1 mm or less in diameter.

\* \* \* \* \*